United States Patent
Sharma

(10) Patent No.: US 6,555,139 B2
(45) Date of Patent: *Apr. 29, 2003

(54) PREPARATION OF MICRON-SIZE PHARMACEUTICAL PARTICLES BY MICROFLUIDIZATION

(75) Inventor: Vinay K. Sharma, Long Valley, NJ (US)

(73) Assignee: Wockhardt Europe Limited, Dublin (IE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/340,917

(22) Filed: Jun. 28, 1999

(65) Prior Publication Data

US 2002/0071870 A1 Jun. 13, 2002

(51) Int. Cl.$^7$ .............................. A61K 9/14; A61K 9/16
(52) U.S. Cl. ...................... 424/489; 514/777; 514/781; 514/951
(58) Field of Search .................................. 424/400, 489

(56) References Cited

U.S. PATENT DOCUMENTS

| | | | | |
|---|---|---|---|---|
| 3,985,868 A | * | 10/1976 | Corey, Jr. et al. .............. | 424/45 |
| 4,107,288 A | | 8/1978 | Oppenheim et al. .......... | 424/22 |
| 4,255,431 A | | 3/1981 | Junggren et al. ............ | 424/263 |
| 4,264,611 A | | 4/1981 | Berntsson et al. .......... | 424/266 |
| 4,282,233 A | | 8/1981 | Vilani ......................... | 424/267 |
| 4,309,405 A | | 1/1982 | Guley et al. ................... | 424/21 |
| 4,374,829 A | | 2/1983 | Harris et al. ................. | 424/177 |
| 4,385,078 A | | 5/1983 | Onda et al. ...................... | 427/3 |
| 4,472,380 A | | 9/1984 | Harris et al. ................. | 424/177 |
| 4,533,562 A | | 8/1985 | Ikegami et al. ................. | 427/3 |
| 4,540,566 A | | 9/1985 | Davis et al. ................... | 424/22 |

(List continued on next page.)

FOREIGN PATENT DOCUMENTS

| | | | |
|---|---|---|---|
| EP | 0005129 B1 | 4/1981 | .......... A61K/31/44 |
| EP | 0540158 A1 | 1/1987 | .......... A61K/31/44 |
| EP | 0240158 B1 | 10/1987 | .......... A61K/31/44 |
| EP | 0249587 | 12/1987 | ............ A61K/9/22 |
| EP | 0268956 B2 | 6/1988 | .......... A61K/31/44 |
| EP | 0275796 B2 | 7/1988 | ............ A61K/9/50 |
| EP | 0302720 A1 | 2/1989 | ......... C07D/401/12 |
| EP | 0484265 A1 | 10/1991 | .......... A61K/31/44 |
| EP | 0533264 a1 | 3/1993 | .......... A61K/31/44 |
| EP | 0566142 | 10/1993 | .......... A61K/47/48 |
| ES | 540.147 | 2/1985 | .......... A61K/31/44 |
| FR | 2608988 | 12/1986 | ............ A61K/9/52 |
| WO | 9505164 A | * 2/1995 | |
| WO | 97/39050 | 10/1997 | |
| WO | 99/38507 | 8/1999 | ........... A61R/31/44 |
| WO | 00/59475 | 12/2000 | ............ A61K/9/14 |

OTHER PUBLICATIONS

Deshpande. A.A., et al., "Development of a Novel Controlled–Release System for Gastric Retention", *Pharmaceutical Research*, 14 (6), pp. 815–819, (Jun. 1997).

(List continued on next page.)

Primary Examiner—James M. Spear
(74) Attorney, Agent, or Firm—Schwegman, Lundberg, Woessner & Kluth, P.A.

(57) ABSTRACT

The present invention relates to a process of microfluidization or wet-micronization of hydrophobic drugs in combination with dextrins such as β-cyclodextrin. The microfluidized particles are useful in controlled swellability, erosion rate-controlled drug delivery systems. The process of microfluidization facilitates reduction of mean particle size of slightly soluble but highly permeable drugs and creates a smooth, latex-like micro-suspension. A blend of swellable polymer and insoluble, hydrophilic excipients granulated with the micro-suspension create a swellable matrix that after compaction erodes uniformly over a 24-hour period. Optimization of drug release is achieved by modification of the geometry of the drug delivery system.

28 Claims, 3 Drawing Sheets

U.S. PATENT DOCUMENTS

| | | | |
|---|---|---|---|
| 4,540,602 A | 9/1985 | Motoyama et al. | 427/213.31 |
| 4,620,008 A | 10/1986 | Brandstroom et al. | 546/271 |
| 4,654,206 A | 3/1987 | Okuda et al. | 424/480 |
| 4,659,716 A | 4/1987 | Villani et al. | 514/290 |
| 4,678,516 A | 7/1987 | Alderman et al. | 106/197.1 |
| 4,690,935 A | 9/1987 | Taylor et al. | 514/356 |
| 4,695,467 A | 9/1987 | Uemura et al. | 424/502 |
| 4,703,038 A | 10/1987 | Garthoff et al. | 514/19 |
| 4,704,285 A | 11/1987 | Alderman | 424/468 |
| 4,708,874 A | 11/1987 | DeHaan et al. | 424/470 |
| 4,713,248 A | 12/1987 | Kjornaes et al. | 424/468 |
| 4,727,064 A | 2/1988 | Pitha | 514/58 |
| 4,728,512 A | 3/1988 | Mehta et al. | 424/458 |
| 4,734,285 A | 3/1988 | Alderman | 424/468 |
| 4,753,801 A | 6/1988 | Oren et al. | 424/465 |
| 4,764,604 A | 8/1988 | Muller | 536/103 |
| 4,765,989 A | 8/1988 | Wong et al. | 424/473 |
| 4,769,027 A | 9/1988 | Baker et al. | 424/493 |
| 4,783,337 A | 11/1988 | Wong et al. | 424/468 |
| 4,786,503 A | 11/1988 | Edgren et al. | 424/443 |
| 4,795,642 A | 1/1989 | Cohen et al. | 424/455 |
| 4,816,264 A | 3/1989 | Phillips et al. | 424/468 |
| 4,828,836 A | 5/1989 | Elge et al. | 424/419 |
| 4,834,985 A | 5/1989 | Elger et al. | 424/488 |
| 4,863,931 A | 9/1989 | Schumacher et al. | 514/290 |
| 4,865,849 A | 9/1989 | Conte et al. | 424/466 |
| 4,880,830 A | 11/1989 | Rhodes | 424/470 |
| 4,892,741 A | 1/1990 | Ohm et al. | 424/479 |
| 4,894,233 A | 1/1990 | Sharma et al. | 424/440 |
| 4,915,952 A | 4/1990 | Ayer et al. | 424/467 |
| 4,927,640 A | 5/1990 | Dahlinder et al. | 424/497 |
| 4,933,186 A | 6/1990 | Ohm et al. | 424/476 |
| 4,940,556 A | 7/1990 | MacFarlane et al. | 264/15 |
| 4,942,040 A | 7/1990 | Ragnarsson et al. | 424/486 |
| 4,942,243 A | 7/1990 | Koh et al. | 548/193 |
| 4,946,685 A | 8/1990 | Edgren et al. | 424/472 |
| 4,946,840 A | 8/1990 | Barrish et al. | 514/211 |
| 4,950,484 A | 8/1990 | Olthoff et al. | 424/464 |
| 4,960,105 A | 10/1990 | Ksander et al. | 514/212 |
| 4,960,482 A | 10/1990 | Gymer et al. | 514/383 |
| 4,960,596 A | 10/1990 | Debregeas et al. | 424/458 |
| 4,963,365 A | 10/1990 | Samejima et al. | 424/46 L |
| 4,963,531 A | 10/1990 | Remington et al. | 514/29 |
| 4,963,545 A | 10/1990 | Sobrist et al. | 514/211 |
| 4,966,768 A | 10/1990 | Michelucci et al. | 424/468 |
| 4,966,772 A | 10/1990 | Ohm et al. | 424/482 |
| 4,967,007 A | 10/1990 | Deshmukh et al. | 564/501 |
| 4,968,507 A | 11/1990 | Zentner et al. | 424/465 |
| 4,968,808 A | 11/1990 | Mosdorf et al. | 548/205 |
| 4,983,598 A | 1/1991 | Covero et al. | 514/211 |
| 4,983,740 A | 1/1991 | Peglion et al. | 546/321 |
| 4,987,144 A | 1/1991 | Kanamaru et al. | 514/383 |
| 4,990,535 A | 2/1991 | Cho et al. | 514/556 |
| 4,992,277 A | 2/1991 | Sangekar et al. | 424/465 |
| 4,994,279 A | 2/1991 | Aoki et al. | 424/494 |
| 4,994,458 A * | 2/1991 | Kilbride, Jr. | |
| 4,996,061 A | 2/1991 | Webb et al. | 424/475 |
| 4,999,189 A | 3/1991 | Kogan et al. | 424/79 |
| 5,000,962 A | 3/1991 | Sangekar et al. | 424/482 |
| 5,002,776 A | 3/1991 | Geoghegan et al. | 424/497 |
| 5,004,613 A | 4/1991 | Radebaugh et al. | 424/465 |
| 5,006,344 A | 4/1991 | Jerzewski et al. | 424/465 |
| 5,008,399 A | 4/1991 | Sedergran | 548/413 |
| 5,015,479 A | 5/1991 | Mulligan et al. | 424/457 |
| 5,024,998 A * | 6/1991 | Bodor | 514/58 |
| 5,039,527 A | 8/1991 | Tabibi et al. | 424/450 |
| 5,047,229 A | 9/1991 | Nahas et al. | 424/10 |
| 5,055,306 A | 10/1991 | Barry et al. | 424/482 |
| 5,070,081 A | 12/1991 | Majid et al. | 514/58 |
| 5,071,642 A | 12/1991 | Lahr et al. | 424/474 |
| 5,073,380 A | 12/1991 | Babu et al. | 424/472 |
| 5,082,669 A | 1/1992 | Shirai et al. | 424/495 |
| 5,085,865 A | 2/1992 | Nayak | 424/472 |
| 5,093,200 A | 3/1992 | Watanabe et al. | 428/407 |
| 5,100,675 A | 3/1992 | Cho et al. | 424/468 |
| 5,118,511 A * | 6/1992 | Horn et al. | |
| 5,118,528 A | 6/1992 | Fessi et al. | 427/213.16 |
| 5,124,340 A | 6/1992 | Jaffe et al. | 514/356 |
| 5,126,333 A | 6/1992 | Martin et al. | 514/58 |
| 5,128,142 A | 7/1992 | Mulligan et al. | 424/457 |
| 5,133,908 A | 7/1992 | Stainmesse et al. | 264/4.1 |
| 5,133,974 A | 7/1992 | Paradissis et al. | 424/480 |
| 5,145,684 A | 9/1992 | Liversidge et al. | 424/489 |
| 5,186,930 A | 2/1993 | Kogan et al. | 424/78.1 |
| 5,198,227 A | 3/1993 | Batista et al. | 424/463 |
| 5,209,933 A | 5/1993 | MacFarlane et al. | 424/494 |
| 5,228,905 A | 7/1993 | Grunewalder et al. | 106/2 |
| 5,273,760 A | 12/1993 | Oshlack et al. | 424/480 |
| 5,275,824 A | 1/1994 | Carli et al. | 424/490 |
| 5,310,917 A | 5/1994 | Auerbach | 540/249 |
| 5,314,697 A | 5/1994 | Kwan et al. | 424/480 |
| 5,324,718 A | 6/1994 | Loftsson | 514/58 |
| 5,338,550 A | 8/1994 | Edgren et al. | 424/473 |
| 5,342,609 A | 8/1994 | Meeh et al. | 424/9 |
| 5,354,564 A | 10/1994 | Borish et al. | 424/490 |
| 5,393,765 A | 2/1995 | Infeld et al. | 514/365 |
| 5,395,626 A | 3/1995 | Kotwal et al. | 424/472 |
| 5,436,011 A | 7/1995 | Dennis et al. | 424/482 |
| 5,439,687 A | 8/1995 | Compassi | 424/468 |
| 5,445,829 A | 8/1995 | Paradissis et al. | 424/480 |
| 5,449,521 A | 9/1995 | Loverecich | 424/489 |
| 5,451,409 A | 9/1995 | Rencher et al. | 424/468 |
| 5,453,280 A | 9/1995 | Moest et al. | 424/458 |
| 5,455,046 A | 10/1995 | Baichwal | 424/457 |
| 5,458,888 A | 10/1995 | Chen | 424/464 |
| 5,462,747 A | 10/1995 | Radebaugh et al. | 424/465 |
| 5,464,633 A | 11/1995 | Conte et al. | 424/480 |
| 5,472,712 A | 12/1995 | Oshlack et al. | 424/480 |
| 5,472,954 A | 12/1995 | Loftsson | 514/58 |
| 5,474,786 A | 12/1995 | Kotwal et al. | 424/472 |
| 5,482,718 A | 1/1996 | Shah et al. | 424/480 |
| 5,487,901 A | 1/1996 | Conte et al. | 424/472 |
| 5,500,227 A | 3/1996 | Oshlack et al. | 424/476 |
| 5,510,118 A | 4/1996 | Bosch et al. | 424/489 |
| 5,512,297 A | 4/1996 | Baichwal | 424/451 |
| 5,516,531 A | 5/1996 | Makino et al. | 424/494 |
| 5,534,270 A | 7/1996 | De Castro | 424/490 |
| 5,549,913 A | 8/1996 | Colombo et al. | 424/472 |
| 5,554,387 A | 9/1996 | Baichwal | 424/488 |
| 5,558,879 A | 9/1996 | Chen et al. | 414/480 |
| 5,582,837 A | 12/1996 | Shell | 424/451 |
| 5,593,694 A | 1/1997 | Hayashida et al. | 424/468 |
| 5,637,309 A | 6/1997 | Tajima et al. | 424/423 |
| 5,645,858 A | 7/1997 | Kotwal et al. | 424/495 |
| 5,650,169 A | 7/1997 | Conte et al. | 424/472 |
| 5,656,291 A | 8/1997 | Olsson et al. | 424/458 |
| 5,656,297 A | 8/1997 | Berstein et al. | 424/484 |
| 5,658,589 A | 8/1997 | Parekh et al. | 424/463 |
| 5,662,935 A | 9/1997 | Motta | 424/465 |
| 5,667,801 A | 9/1997 | Baichwal | 424/457 |
| 5,667,804 A | 9/1997 | Wong et al. | 424/472 |
| 5,672,359 A | 9/1997 | Digenis et al. | 424/463 |
| 5,674,521 A | 10/1997 | Gehrke et al. | 424/423 |
| 5,681,582 A | 10/1997 | Gilis et al. | 424/468 |
| 5,681,583 A | 10/1997 | Conte et al. | 424/472 |
| 5,683,716 A | 11/1997 | Hata et al. | 424/451 |
| 5,697,922 A | 12/1997 | Thombre | 604/892.1 |
| 5,733,568 A | 3/1998 | Ford | 424/433 |
| 5,738,874 A | 4/1998 | Conte et al. | 424/472 |

| | | |
|---|---|---|
| 5,756,123 A | 5/1998 | Yamamoto et al. .......... 424/451 |
| 5,773,025 A | 6/1998 | Baichwal ..................... 424/458 |
| 5,776,501 A | 7/1998 | Kokubo et al. ............. 424/494 |
| 5,780,057 A | 7/1998 | Conte et al. ................ 424/468 |
| 5,788,987 A | 8/1998 | Bustti et al. ................ 424/480 |
| 5,807,579 A | 9/1998 | Vilkov et al. ............... 424/469 |
| 5,824,341 A | 10/1998 | Seth et al. .................. 424/473 |
| 5,827,852 A | 10/1998 | Russell et al. .............. 514/255 |
| 5,834,496 A | 11/1998 | Young ........................ 514/356 |
| 5,834,497 A | 11/1998 | Fagher et al. ............... 514/356 |
| 5,837,379 A | 11/1998 | Chen et al. ................. 424/465 |
| 5,846,563 A | 12/1998 | Baichwal ..................... 424/457 |
| 5,849,329 A | 12/1998 | Conte et al. ................ 424/469 |
| 5,849,330 A | 12/1998 | Marvola et al. ............ 424/472 |
| 5,855,914 A | 1/1999 | Koyama et al. ............ 424/494 |
| 5,858,409 A | 1/1999 | Karetny et al. ............. 424/489 |
| 5,869,029 A | 2/1999 | Graff-Andersen et al. .... 424/52 |
| 5,871,776 A | 2/1999 | Mehta ........................ 424/462 |
| 5,876,754 A | 3/1999 | Wunderlich et al. ........ 424/489 |
| 5,877,175 A | 3/1999 | Sergent et al. .............. 514/252 |
| 5,885,615 A | 3/1999 | Chouinard et al. ......... 424/465 |
| 5,891,474 A | 4/1999 | Busetti et al. .............. 424/490 |
| 5,895,663 A | 4/1999 | Irwin et al. ................. 424/468 |
| 5,897,910 A | 4/1999 | Rosenberg et al. ........ 427/2.14 |
| 5,902,606 A * | 5/1999 | Wunderlich et al. |
| 5,916,590 A | 6/1999 | Cody et al. ................. 424/452 |
| 5,916,592 A | 6/1999 | Parekh et al. ............... 424/464 |
| 5,919,481 A | 7/1999 | Cody et al. ................. 424/452 |
| 5,922,352 A | 7/1999 | Chen et al. ................. 424/465 |
| 5,939,099 A | 8/1999 | Grabowski et al. ......... 424/488 |
| 5,942,624 A | 8/1999 | Gustavsson et al. ........ 546/321 |
| 5,945,125 A | 8/1999 | Kim .......................... 424/473 |
| 5,958,456 A | 9/1999 | Biachwall et al. .......... 424/489 |
| 5,965,163 A | 10/1999 | Miller et al. ................ 424/468 |
| 5,965,167 A | 10/1999 | Sanghvi et al. ............. 424/490 |
| 5,968,554 A | 10/1999 | Beiman et al. ............. 424/480 |
| 5,977,369 A | 11/1999 | Desai et al. ................ 546/321 |
| 5,997,906 A | 12/1999 | Wood et al. ................ 424/494 |
| 5,998,445 A | 12/1999 | Souda et al. ................ 514/338 |
| 6,004,582 A | 12/1999 | Faour et al. ................ 424/473 |
| 6,039,976 A | 3/2000 | Mehra et al. ............... 424/480 |
| 6,048,548 A | 4/2000 | Baichwal ..................... 424/468 |
| 6,051,585 A | 4/2000 | Weinstein et al. .......... 514/335 |
| 6,083,533 A | 7/2000 | Cremer ....................... 424/472 |
| 6,096,339 A | 8/2000 | Ayer et al. .................. 424/473 |
| 6,100,274 A | 8/2000 | Kou .......................... 514/290 |
| 6,103,263 A | 8/2000 | Lee et al. ................... 424/468 |
| 6,110,927 A | 8/2000 | Buckland et al. ........... 514/290 |
| 6,120,802 A | 9/2000 | Breitenbach et al. ....... 424/464 |
| 6,132,758 A | 10/2000 | Munayyer et al. .......... 424/439 |
| 6,183,778 B1 | 2/2001 | Conte et al. ................ 424/472 |
| 6,251,427 B1 | 6/2001 | Kim et al. .................. 424/451 |
| 6,258,381 B1 | 7/2001 | Luber et al. ................ 424/464 |

OTHER PUBLICATIONS

Rowe, R.C., "Chapter 12: 'Defects in Acqueous Film Coated Tablets, In: Aqueous Polymeric Coatings for Pharmaceutical Dosage Forms', Second Edition, James W. McGininity, Ed.", Published by Marcel Dekker, Inc., New York, pp. 419–440, (1997).

Rowe, R.C., et al., "Effect of polymer molecular weight on the incidence of film cracking and spliting on film coated tablets", J. Pharm. Pharmacol., 32 (8), pp. 583–586, (Aug. 1980).

Sangekar, S.A., et al., "Effect of moisture on physical characteristics of tablets prepared from direct compression excipients", J. Pharm. Sci., 61, pp. 939–944, (Jun. 1972).

"Felodipine", British Pharmacopoeia, (London: The Stataionary Office), 574–575, (Dec. 1, 1998).

Aithal, K.S., et al., "Molecular Modeling for the Interaction Between Certain Drugs with Betacyclodextrin", Indian J. Phar. Sci., vol. 60 (2), 68–72, (1998).

Lipinsky, C.A., et al., "Experimental and computational approaches to estimate solubility and permeability in drug discovery and development settings", Advanced Drug Delivery Reviews, vol. 23, 3–25, (1997).

Sharma, A., et al., "Activity of Paclitaxel Liposome Formulations Against Human Ovarian Tumor Xenografts", Int. J. Cancer, vol. 71, 103–107, (1997).

Szejtli, J., "Cyclodextrins in Drug Formulations: Part I", Pharmaceutical Technology, (Jun. 1991).

Uekama, K., et al., "New perspectives in Cyclodextrin Pharmaceutical Applications. Cyclodextrin Derivatives as New Drug Carriers", Drug Invest., vol. 2, 22, (1990).

U.S. patent application Ser. No. 09/697,670, filed Oct. 26, 2000, titled "Composition of Excipients for In Vitro Stabilization of Felodipine in a Controlled Release Formulation."

U.S. patent application Ser. No. 09/765,726, filed Jan. 18, 2001, titled, "Preparation of Micron–Size Felodipine Particles by Microfluidization."

Bode, H., et al., "Investigation of Nifedipine Absorption in Different Regions of the Human Gastrointestinal (GI) Tract After Simultaneous Administration of $^{13}$C– and $^{12}$C–nifiedipine", European Journal of Clinical. Pharmacology, 50 (3), 195–201, (1996).

Bodmeier, R., et al., "Indomethacin Polymeric Nanosuspensions Prepared by Microfluidization", Journal of Controlled Release, 12(3), 223–233, (May, 1990).

Bodmeier, R., et al., "Spontaneous Formation of Drug–Containing Acrylic Nanoparticles", Journal of Microencapsulation, 8 (2), 161–170, (1991).

Buri, P., et al., "Formulation of Sustained–release Tablets, II. Hydrophillic Matrices", Pharmaceutica Acta Helvetiae, 55 (7–8), 189–197, (1980) in French.

Gregoriadis, G., et al., "A Procedure for the Efficient Entrapment of Drugs in Dehydration–Rehydration Liposomes (DRVs)", International Journal of Pharmaceutics, 65 (3), 235–242, (1990).

Koosha, F., et al., "Nanoparticle Production by Microfluidization", Archiv Der Pharmazie, 321 (9), p. 680, (1988).

Lidgate, D.M., et al., "Sterile Filtration of a Parenteral Emulsion", Pharmaceutical Research, 9 (7), 860–863, (1990).

Lidgate, M., et al., "Formulation of Vaccine Adjuvant Muramyldipeptides. Part 3. Processing Optimization, Characterization and Bioactivity of an Emulsion Vehicle", Pharmaceutical Research, 6(9), 748–752, (1989).

Reynolds, J.E., "Martindale, the Extra Pharmacopeia", Royal Pharmaceutical Society, London, Nutritional Agents and Vitamins, p. 1262, (1989), Talsma, H., et al., "The Size Reduction of Liposome With a High Pressure Homogenizer (Microfluidizer) : Characterization of Prepared Dispersions and Comparison With Conventional Methods", Drug Development and Industrial Pharmacy, 15(12), 197–207, (1989).

* cited by examiner

PREPARATION OF MICRON-SIZE PHARMACEUTICAL PARTICLES BY MICROFLUIDIZATION

BACKGROUND OF THE INVENTION

1. Field of the Invention

The present invention relates to processes for preparing small particles, preferably spherical particles, usually in the range of about 1 to 30 microns, with the size controllable in narrow ranges of from 1–5 micrometers, 5–15 micrometers, or 15 to 30 micrometers. These particles, referred to herein as "micronized particles," have the advantage of controlled sizing, even size distribution of particles, controlled dissolution rates, and more consistent drug release properties. The invention also relates to new micronized particles obtained by the process of the invention and to their use in human or animal pharmacy. The present invention also relates to a process for the microfluidization of hydrophobic drugs and the use of the microfluidized product in a drug delivery system to provide controlled swellability and erosion-rate control. The drug release properties may also be modified as desired by using the microfluidization process to alter the product (pellet or particle) design or geometry.

2. Background of the Art

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 15 mg/ml or less than 10 mg/ml, tend to be eliminated from the gastrointestinal tract before being absorbed into the circulation. Moreover, poorly water soluble drugs tend to be unsafe for intravenous administration techniques, which are used primarily in conjunction with fully soluble drug substances.

It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. For example, dry milling techniques have been used to reduce particle size and hence influence drug absorption. However, in conventional dry milling, as discussed by Lieberman et al, *Pharmaceutical Dosage Forms: Tablets*, Volume 2, Chapter 3, "Size Reduction", p. 132, (1990), the limit of fineness is reached in the region of 100 microns (100,000 nm) when material cakes on the milling chamber. Lachman et al note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airjet milling techniques have provided particles ranging in average particle size from as low as about 1 to 50 .mu.m (1,000–50,000 nm). However, such dry milling techniques can cause unacceptable levels of dust.

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptably large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process. U.S. Pat. No. 4,540,602 (Motoyama et al) discloses a solid drug pulverized in an aqueous solution of a water-soluble high molecular substance using a wet grinding machine. However, Motoyama et al teach that as a result of such wet grinding, the drug is formed into finely divided particles ranging from 0.5 .mu.m (500 nm) or less to 5 .mu.m (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible non-solvent for the substance and results in the formation of non-crystalline nanoparticles. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmacodynamically active material. However, the particles comprise a crosslinked matrix of macromolecules having the active material supported on or incorporated into the matrix.

U.S. Pat. No. 5,145,684 discloses a process for preparing particles consisting of a crystalline drug substance having a surface modifier or surface active agent adsorbed on the surface of the particles in an amount sufficient to maintain an average particle size of less than about 400 nanometers. The process of preparation comprises the steps of dispersing the drug substance in a liquid dispersion medium and applying mechanical means in the presence of grinding media to reduce the particle size of the drug substance to an average particle size of less than 400 nm. The particles can be reduced in the presence of a surface active agent or, alternatively, the particles can be contacted with a surface active agent after attrition. The presence of the surface active agent prevents flocculation/agglomeration of the nanoparticles.

The mechanical means applied to reduce the particle size of the drug substance is a dispersion mill, the variety of which include a ball mill, an attrition mill, a vibratory mill and media mill, such as sand mill, and a bead mill.

The grinding media for the particle size reduction is spherical or particulate in form and includes: ZrO.sub.2 stabilized with magnesia, zirconium silicate, glass, stainless steel, titania, alumina and ZrO.sub.2 stabilized with yttrium. Processing time of the sample can be several days long. This patent is incorporated herein in its entirety by reference.

To a more limited extent the prior art also utilized microfluidizers for preparing small particle-size materials in general. Microfluidizers are relatively new devices operating on the submerged jet principle. In operating a microfluidizer to obtain nanoparticulates, a premix flow is forced by a high pressure pump through a so-called interaction chamber consisting of a system of channels in a ceramic block which split the premix into two streams. Precisely controlled shear, turbulent and cavitational forces are generated within the interaction chamber during microfluidization. The two streams are recombined at high velocity to produce shear. The so-obtained product can be recycled into the microfluidizer to obtain smaller and smaller particles.

The prior art has reported two distinct advantages of microfluidization over conventional milling processes (such as reported in U.S. Pat. No. 5,145,684, supra): substantial reduction of contamination of the final product, and the ease of production scaleup.

Numerous publications and patents were devoted to emulsions, liposomes and/or microencapsulated suspensions of various substances including drug substances produced by the use of microfluidizers. See, for example:

1) U.S. Pat. No. 5,342,609, directed to methods of preparing solid apatite particles used in magnetic resonance imaging, x-ray and ultrasound.

2) U.S. Pat. No. 5,228,905, directed to producing an oil-in-water dispersion for coating a porous substrate, such as wood.

3) U.S. Pat. No. 5,039,527 is drawn to a process of producing hexamethyhnelamine containing parenteral emulsions.

4) G. Gregoriadis, H. Da Silva, and A. T. Florence, "A Procedure for the Efficient Entrapment of Drugs in Dehydration-Rehydration Liposomes ODRVs), Int. J. Pharm. 65, 235–242 (1990).

5) E. Doegito, H. Fessi, M. Appel, F. Puisieux, J. Bolard, and J. P. Devissaguet, "New Techniques for Preparing Submicronic Emulsions—Application to Amphotericine-B,: STP Pharma Sciences 4, 155–162 (1994).

6). M. Lidgate, R. C. Fu, N. E. Byars, L. C. Foster, and J. S. Fleitman, "Formulation of Vaccine Adjuvant Muramyldipeptides. Part 3. Processing Optimization, Characterization and Bioactivity of an Emulsion Vehicle," Pharm Res. 6, 748–752 (1989).

7) H. Talsma, A. Y. Ozer, L. VanBloois, and D. J. Crommelin, "The Size Reduction of Liposomes with a High Pressure Homogenizer (Microfluidizer): Characterization of Prepared Dispersions and Comparison with Conventional Methods," Drug Dev. Ind. Pharm. 15, 197–207 (1989).

8) D. M. Lidgate, T. Tranner, R. M. Shultz, and R. Maskiewicz, "Sterile Filtration of a Parenteral Emulsion," Pharm. Res. 9, 860–863 (1990).

9) R. Bodmeier, and H. Chen, "Indomethacin Polymeric Nanosuspensions Prepared by Microfluidization," J. Contr. Rel. 12, 223–233 (1990).

10) R. Bodmeier, H. Chen, P. Tyle, and P. Jarosz, "Spontaneous Formation of Drug-Containing Acrylic Nanoparticles," J. Microencap, 8, 161–170 (1991).

11) F. Koosha, and R. H. Muller, "Nanoparticle Production by Microfluidization," Archiv Der Pharmazie 321,680 (1988).

However, reports are few on reducing mean particle size (hereinafter sometimes abbreviated as MPS) of water-insoluble materials for use in pharmaceutical/diagnostic imaging compositions.

It is known from the prior art, described in Patent FR 2,608,988, to prepare particles smaller than 500 nm in size by at least three types of process. The first process type consists of polymerization of a monomer in a solution so as to obtain a micellar dispersion of the polymer in the solution. This first process type is limited to monomers which can be polymerized in solution. Moreover, it necessitates removal, after the polymerization step, of the polymerization catalyst, the low molecular weight oligomers, the monomers and the surfactants needed for the polymerization. The polymer obtained in this first process type has a random molecular weight distribution.

The second and third process types use preformed polymers, dissolving them in a solvent, forming a precipitate or a dispersion from a solution of these polymers and a non-solvent, and then evaporating off the solvent to recover the nanoparticles in the form of a colloidal suspension. The solvent solution is generally an organic solution of the polymer, and the nonsolvent solution is often an aqueous solution.

According to the second type of process, the polymer is dissolved in a water-miscible organic solvent. When the resulting solution is mixed with the aqueous phase, the polymer insoluble in the aqueous phase/organic solvent mixture precipitates in the form of nanoparticles.

According to the third type of process, a water immiscible organic solvent containing the polymer is emulsified in an aqueous phase, and the organic solvent is then evaporated off.

Formation of the precipitate or the emulsion requires the presence of a considerable amount of surfactant. It is very difficult to remove the surfactant remaining in the colloidal suspension during the subsequent evaporation to obtain the nanoparticles. Furthermore, the presence of a surfactant is often undesirable in the interest of good biocompatibility. Hence the latter two techniques cannot be used for the preparation of biocompatible nanoparticles because a colloidal protective agent is present.

FR 2,608,988 relates to a process for preparing dispersible colloidal systems in the form of nanoparticles smaller than 500 nm. These nanoparticles, based on a substance which can be a polymer and/or an active principle, are obtained by the second method mentioned above. The nanoparticles which are obtained, based on a polylactic polymer, contain an amount of surfactant equal to the amount of polymer in the majority of the examples. In only one example (Example 4) does the inventor claim to obtain nanoparticles of polylactic polymer without a surfactant. The Applicants reproduced this experiment and obtained nanoparticles of polylactic polymer from an acetone solution of polylactic acid and water with extremely low yields, always less than 10%. Hence this technique cannot practicably be used for the preparation of nanoparticles of polylactic acid in the absence of a surfactant.

U.S. Pat. No. 5,510,118 describes a process of preparing stable, dispersible, water-insoluble, drug nanoparticles consisting essentially of a crystalline drug substance having a surface modifier adsorbed on the surface thereof comprising the steps of:

a) dispersing a crystalline drug substance in a liquid dispersion medium containing a surface modifier, and
b) subjecting the liquid dispersion medium to the comminuting action of a microfluidizer asserting shear, impact and cavitation forces onto the crystalline drug substance contained in the liquid dispersion medium for a time necessary to reduce the mean particle size of said crystalline drug substance to less than 400 nm. The patent asserts that the particles can be formulated into pharmaceutical compositions exhibiting remarkably high bioavailability, the process provides a stable dispersion consisting essentially of a liquid dispersion medium and the above-described particles dispersed therein, and in a particularly valuable and important embodiment of the invention, there is provided a pharmaceutical composition comprising the above-described particles and a pharmaceutically acceptable carrier therefor. Such pharmaceutical composition is useful in a method of treating mammals. It is also an asserted advantage that a wide variety of surface modified drug nanoparticles free of unacceptable contamination can be prepared in accordance with this invention and that pharmaceutical compositions containing poorly water soluble drug substances are provided which are suitable for intravenous administration techniques. The particle size is therefore always reduced to less than 0.4 micrometers to assure rapid absorption of the active drug by the blood stream upon intravenous delivery.

U.S. Pat. No. 5,534,270 describes a process for preparing sterilized nanoparticulate crystalline drug particles comprising the steps of:

1) providing a drug substance having a solubility in water of less than 10 mg/ml
2) depyrogenating rigid grinding media having an average particle size less than 3 mm at from 200.degree° C. to 300° C. for from 6 to 20 hours
3) mixing the drug substance and rigid grinding media and autoclaving it from 100.degree° C. to 150° C. for 10 to 50 minutes and
4) adding a surface modifier to the autoclaved drug substance and rigid grinding media to a dispersion medium and wet grinding the drug substance sufficiently to maintain an effective average particle size of less than 400 nm. The particle size is therefore always reduced to less than 0.4 micrometers to assure rapid absorption of the active drug by the blood stream upon intravenous delivery.

BRIEF SUMMARY OF THE INVENTION

The present invention describes a process for providing particles or crystal particles of pharmaceutically active agents that have low levels of water solubility (e.g., less than 15 mg/ml) by microfluidization of the pharmaceutically active agents. The particles of pharmaceutically active agents are provided in dimensions for use in oral ingestion of the pharmaceutically active agents where the particle size must be controlled within defined micron dimension ranges (e.g., above 0.5 microns [up to about 20 microns] or between 1.0 and 15 microns). In the presence of dextrins, particularly cyclodextrins, particle sizes even in the nanometer ranges (e.g., below 1000 nm, e.g., less than 500 nm, less than 400 nm, and between 20 and 1000, or between 30 and 500 nm are novel and may be produced according to the present invention (with or without the presence of surface active agents or surface modifying agents). The pharmaceutically active agents may be microfluidized in the absence of any other pharmaceutically active coingredients (e.g., excipients, binding agents, surfactants or surface modifying ingredients or with their use). One ingredient that has been found to be beneficial in microfluidization of some pharmaceutically active agents has been cyclodextrins, such as beta-cyclodextrin. These cyclodextrins are provided into the stream to be microfluidized as particles and remain as particles through the conclusion of the microfluidization process. The particle size distribution effected by this process is quite uniform and controllable.

Significant process advantages are provided by the use of the dextrins, and definite product advantages occur with the use of the dextrins. It is to be noted that the dextrin(s) is added to the hydrophobic pharmaceutical as a solid and at least some of the dextrin(s) remains as a solid throughout the entire microfluidization process. The dextrin may be left with the pharmaceutical drug in the dosage product or either physically removed or removed by differential dissolution in a liquid medium that is not a solvent for the pharmaceutical.

DETAILED DESCRIPTION OF THE INVENTION

Figure 1:
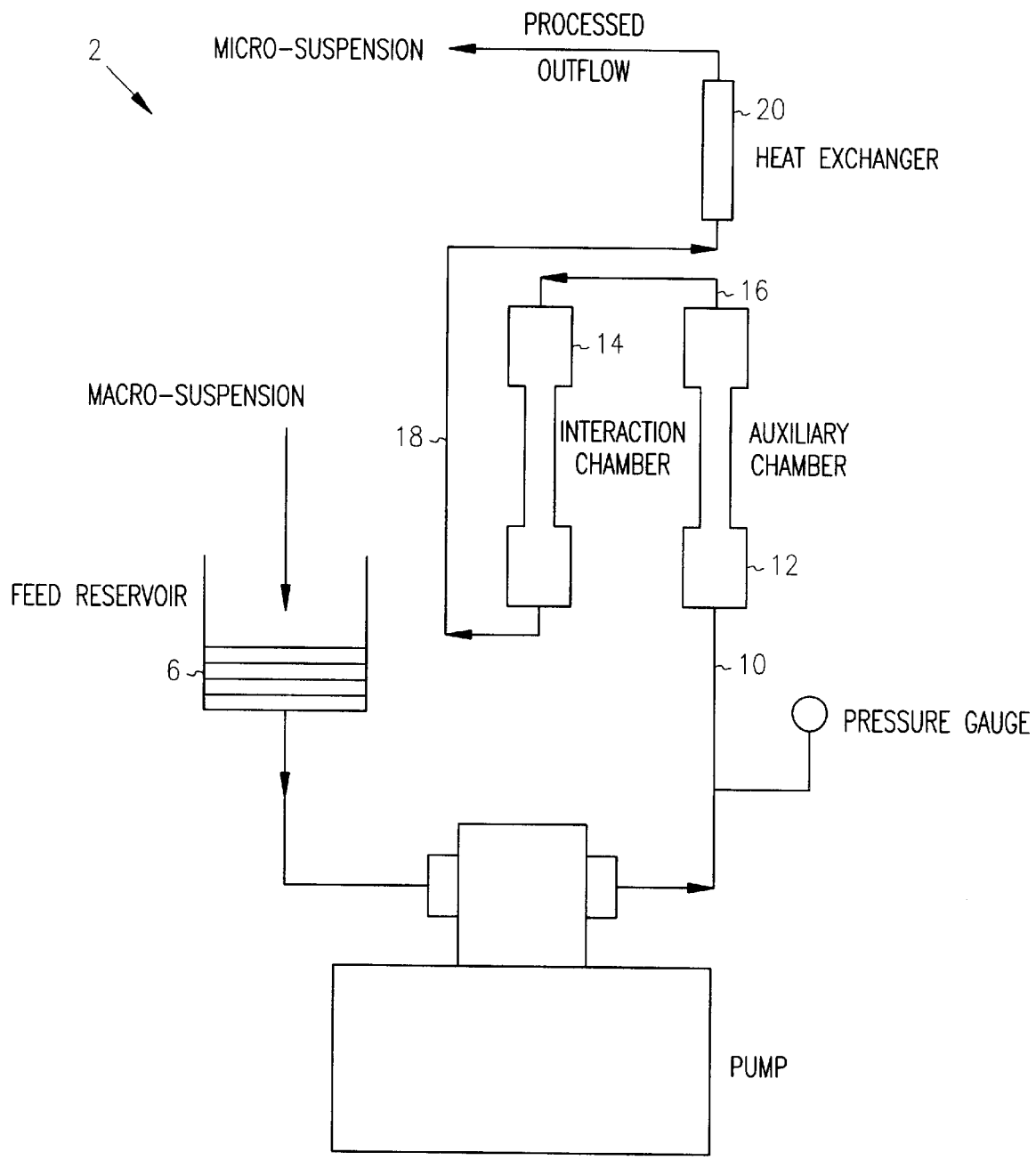
FIG. 1 shows a schematic of a commercial microfluidization system useful in the practice of the present invention.
Figure 2:
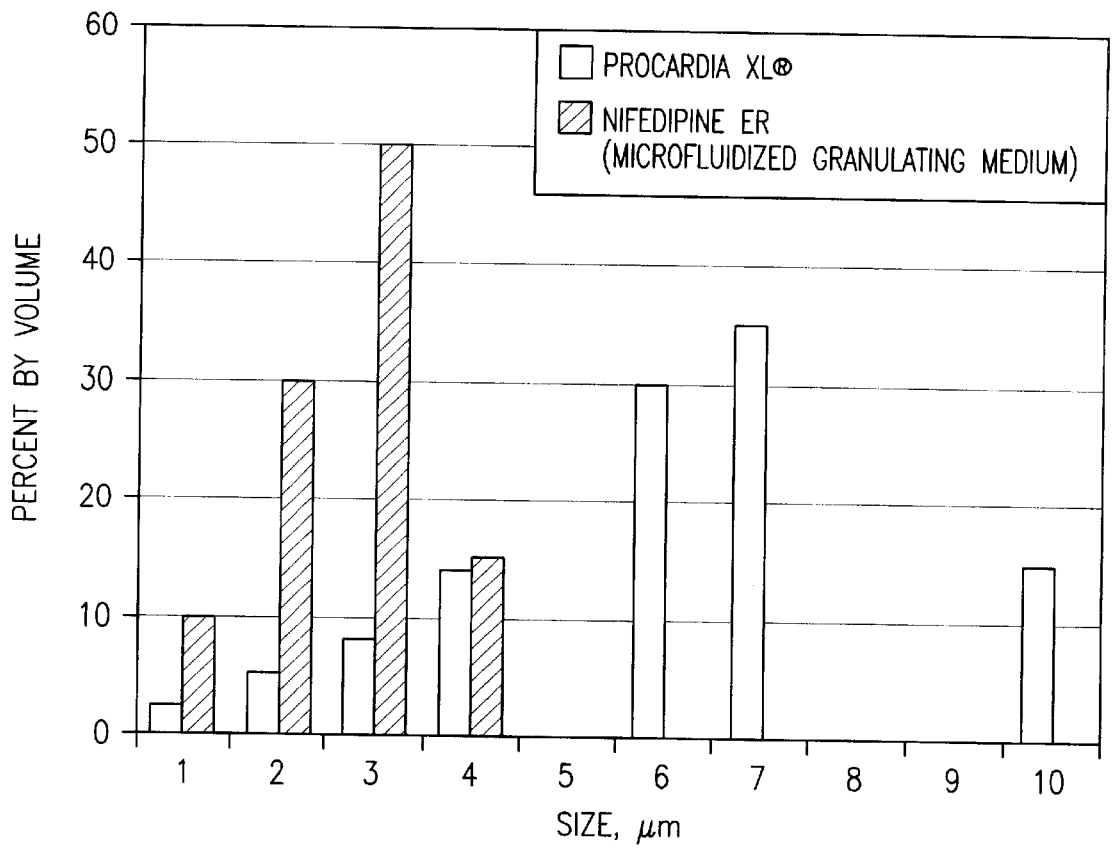
FIG. 2 shows a graphic comparison of the size distribution of Nifedipine ER particles made by the practice of the present invention and a commercially available composition, Procardia XL(R).
Figure 3:
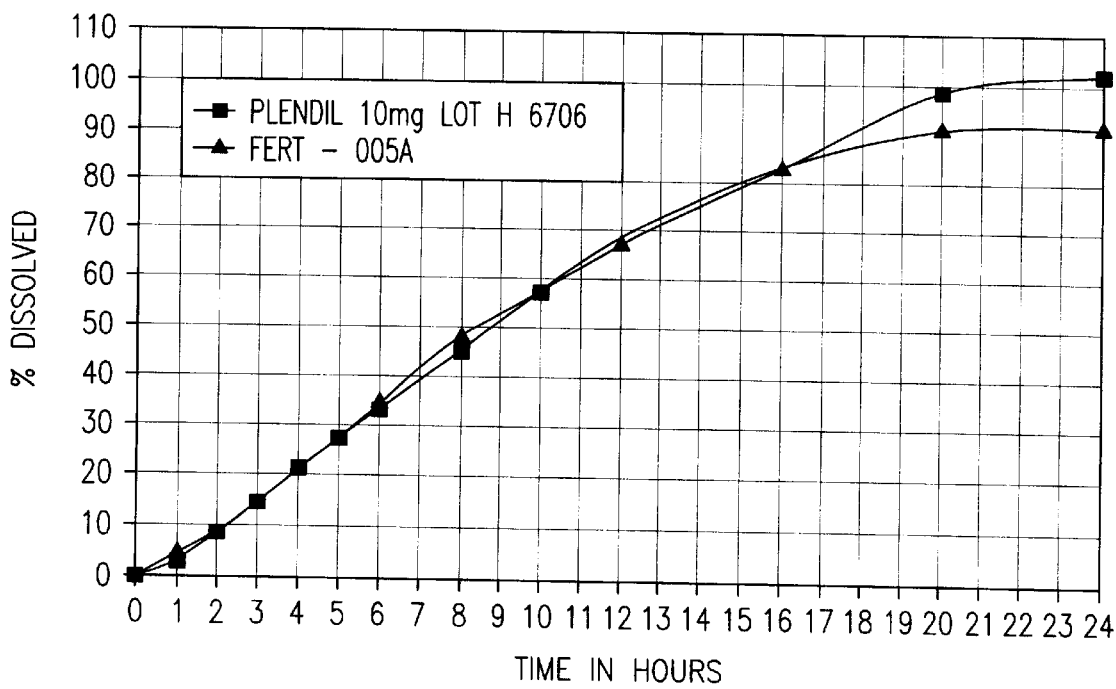
FIG. 3 shows comparative dissolution profiles for commercially available Plendil$^{(R)}$, 10 mg, lot H 6706 and a microfluidized Felodipine (average particle size 7 microns, weight average particle size) and beta-cyclodextrin according to the present invention in 500 ml of an aqueous solution comprising phosphate buffer, pH 6.5, 1% by weight sodium lauryl sulfate, with stirring.
Figure 4:
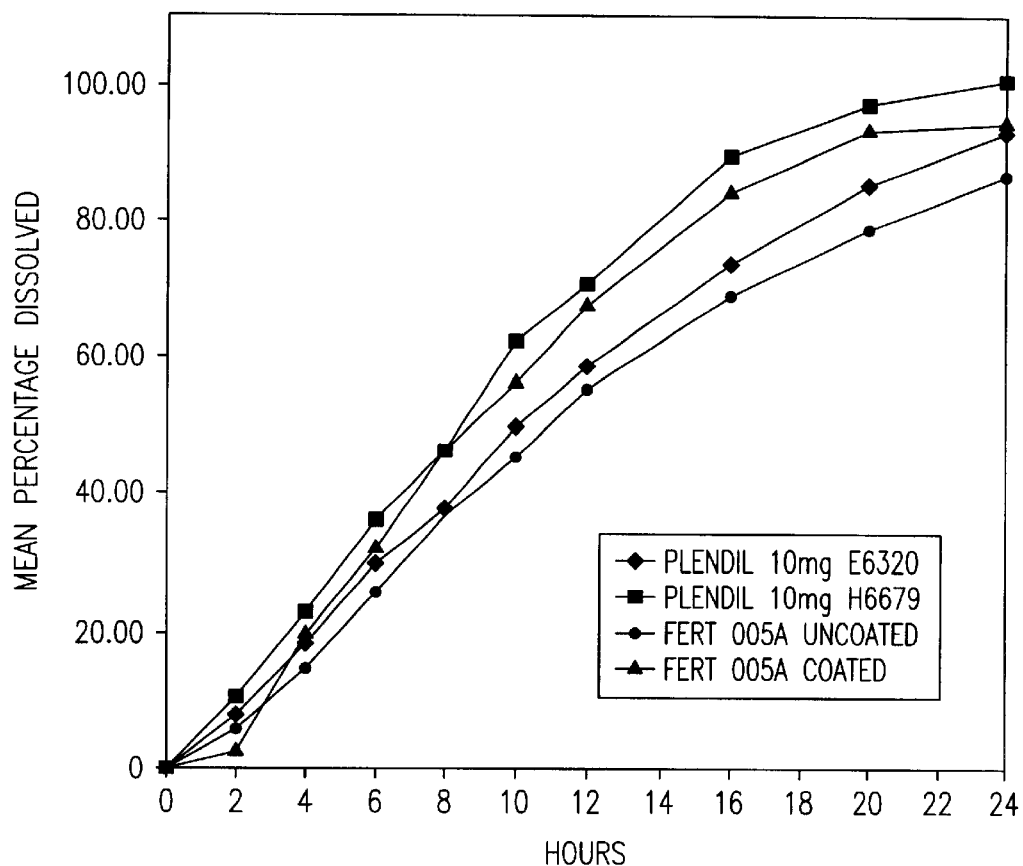
FIG. 4 shows comparative dissolution profiles for two commercially available Plendil$^{(R)}$ (10 mg, lots H 6320 and H 6679) and two microfluidized Felodipine samples (average particle size 7 microns, weight average particle size) and beta-cyclodextrin (FERT 005A, uncoated and FERT 005A coated) according to the present invention in 500 ml of an aqueous solution comprising phosphate buffer, pH 6.5, 1% by weight sodium lauryl sulfate, with stirring.
Figure 5:
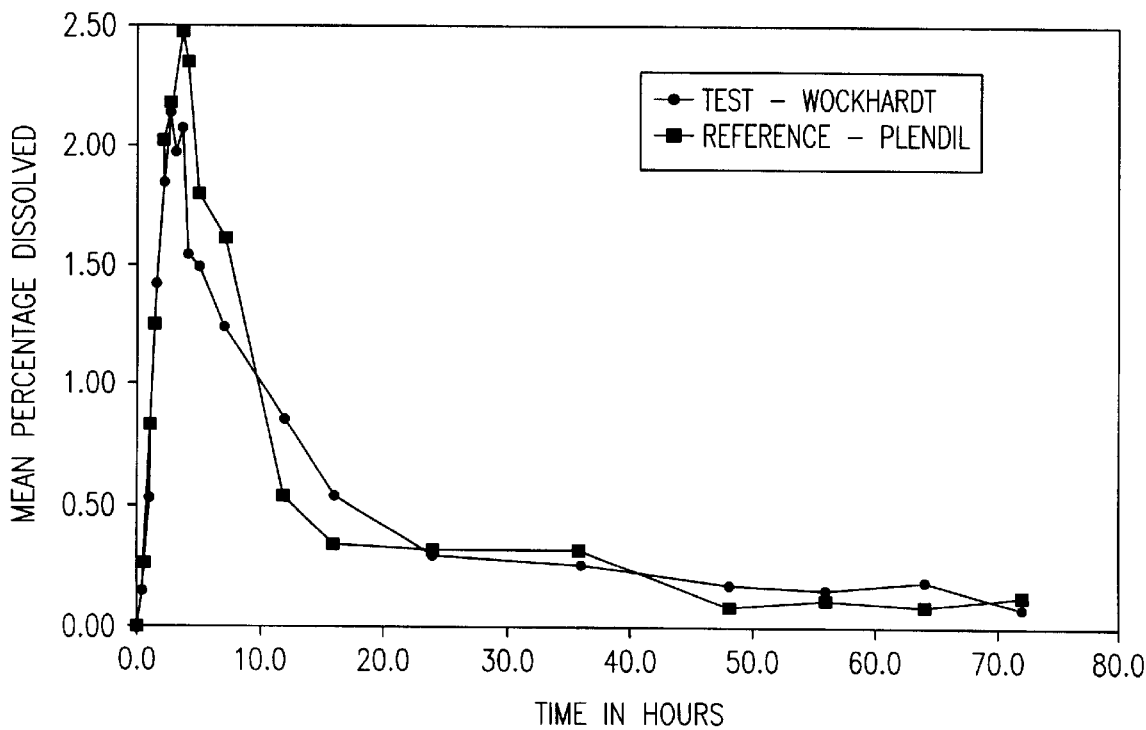
FIG. 5 shows the bioequivalence of Felodipine ER tablets (10 mg) for commercially avaiable Plendil and a test tablet manufactured according to the practice of the present invention, without optimization of the formulation.

The invention can be practiced with a wide variety of drug substances. The drug substance preferably is present in an essentially pure form. The drug substance must be poorly soluble and dispersible in at least one liquid medium. By "poorly soluble" it is meant that the drug substance has a solubility in the liquid dispersion medium, e.g. water, of less than about 15 mg/ml, less than 10 mg/ml, and preferably of less than about 1 mg/ml. A preferred liquid dispersion medium is water. However, the invention can be practiced with other liquid media in which a drug substance is poorly soluble and dispersible including, for example, aqueous salt solutions, safflower oil and solvents such as ethanol, t-butanol, hexane and glycol. The pH of the aqueous dispersion media can be adjusted by techniques known in the art.

Suitable drug substances can be selected from a variety of known classes of drugs including as long as the drugs are hydrophobic and relatively insoluble as defined herein. For example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anoretics, sympathomimetics, thyroid agents, vasodilators and xanthines are among the classes of hydrophobic and relatively water-insoluble drugs that may be used. Preferred drug substances include those intended for oral administration. A description of these classes of drugs and a listing of species within each class can be found in Martindale, The Extra Pharmacopoeia, Twenty-ninth Edition, The Pharmaceutical Press, London, 1989, the disclosure of which is hereby incorporated herein by reference in its entirety. The drug substances are commercially available and/or can be prepared by techniques known in the art.

As indicated, the primary forces attributed to microfluidization by the microfluidizer for producing either emulsions or dispersions, and for reducing mean particle size of water-insoluble materials are:

a) shear, involving boundary layers, turbulent flow, acceleration and change in flow direction;

b) impact, involving collision of the particles processed with solid elements of the microfluidizer, and collision between the particles being processed; and c) cavitation, involving an increased change in velocity with a decreased change in pressure, and turbulent flow. An additional force can be attributed to attrition, i.e., grinding by friction.

The M-110Y laboratory scale microfluidizer consists of an air motor connected to a hydraulic pump which circulates the process fluid. The formulation stream is propelled at high pressures (up to 23,000 psi) through a specially designed interaction chamber which has fixed microchannels that focus the formulation stream and accelerate it to a high velocity. Within the chamber the formulation is subjected to intense shear, impact and cavitation, all of which contribute to particle size reduction. After processing, the formulation stream is passed through a heat exchanger coil and can be collected or recirculated through the machine. The microfluidizer was typically used in a continuous processing mode for up to three hour of total processing time. The heat exchanger and interaction chamber were externally cooled with a refrigerated circulating water bath.

The use of microfluidization in pharmaceutical dosage form development has largely been limited to processing of emulsions or liposomes as previously discussed, except for U.S. Pat. Nos. 5,510,118 and 5,534,270, wherein only nanosize particles (e.g., less than 0.5 micrometers or less than 500 nanometers) are produced by coating the particles with a surface modifying agent and repeatedly passing the particles through the microfluidizer. However, reports are few on reducing mean particle size (hereinafter sometimes abbreviated as MPS) of water-insoluble materials for use in pharmaceutical/diagnostic imaging compositions. Additionally, Applicants are aware of no reported work on hydrophilic drug delivery systems for hydrophobic drugs where the particle size of the hydrophobic drugs is controlled discretely at about 1–3 micrometers (e.g., 0.8 to 5 microns), about 6–12 micrometers (e.g., 5–14 microns), and about 15–30 micrometers (e.g., 14–32 microns). It is also an aspect of the present invention to provide these different size range of particles of the hydrophobic drug in achieving multiple input functions, respectively representing fast, medium and slow rates of drug release with such hydrophobic drug particles.

There are a number of characteristics of the disclosure and process of U.S. Pat. Nos. 5,510,118 and 5,534,270 that are noteworthy in comparison to the present invention. Those references require the presence of the surface modifying material (usually a surfactant or water soluble polymer) in sufficient amounts to coat (e.g., physically adhere but not chemically bond) the surface of the particles and maintain an effective particle size of less than 400 nm. The individually absorbed molecules of the surface modifier are also clearly identified as essentially free of intermolecular crosslinkages. As can be seen, the surface modifiers of U.S. Pat. Nos. 5,510,118 and 5,534,270 cannot remain as distinct particles adjacent to the pharmaceutical particles. Although U.S. Pat. Nos. 5,510,118 and 5,534,270 are singularly void of any definition of the term surface modifiers or their specific function, it appears that the materials act as mediating or coupling agents to the aqueous environment, and, in all likelihood act as size moderating agents, probably by some dissolution reprecipitation phenomenon. The amount of surface modifier used also appears to be above the critical micelle concentration (CMC) for each of the surface modifying agents. Although this CMC varies for each surfactant, the levels or percentages at which the surface modifying agents are used (see the examples, with w/w percentages of about 0.2 to 5% in Table I of U.S. Pat. No. 5,510,118) appear to be consistent with at least threshhold CMC levels. In the present invention, surface active agents are not required, where surface active agents are used, they may be used below critical micelle concentrations (e.g., less than 0.2% w/w of solution/dispersion, less than 0.1% w/w of solution/dispersion, or less than 0.05% w/w of solution/dipsersion) while even optimizing the process. In fact, with certain pharmaceuticals, particularly in the manufacture of micronized Felodipine, the absence of any surface active agents (e.g., less than 0.05% w/w or less than 0.01% w/w of surface active agent) is preferred.

This feature, particularly with respect to Felodipine, is particularly indicative of the unique benefits of the invention. One commercially available form of Felodipine (Plendil$^{(R)}$ 500 mg) is provided with a very high level of surface active agent, on the order of 90/10% w/w pharmaceutical to surface active agent to enable the drug to be bioavailable and/or soluble. The ability to provide the present method for providing particles of Felodipine that have less than 10%, less than 5%, less than 1%, and less than 0.2% surface active agent or be completely free of surface active agent, yet have them in an equivalently bioavailable form, is quite surprising.

The formation of micronized particles of a pharmaceutical active principle may be performed in the absence of all materials, except for the fluid carrier, which may be introduced either into the carrier or in a precipitation solvent. The process is designed for use with pharmaceutically active principals or agents that have limited solubility in the carrier solution, e.g., water. By limited solubility it is meant that the agents has a solubility less than 15 mg/ml, more preferably less than 12 mg/mg, and more preferably less than 10 mg/ml. The agent may actually be completely insoluble in water. Although it is still possible to form micronized if the active principle is soluble in water, the yield thereof may be reduced. The micron size particles generally have an average diameter of between 1.0 and 15 micrometers, and preferably an average diameter of between 1 and 12 or 1 and 10 micrometers.

The particles obtained may be used in many fields, such as agrochemistry, reprography paper and photographic paper but, as a result of their fully biocompatible nature, are intended more especially for the human or animal pharmaceutical industry, particularly in the field of oral administration. For micronized feed materials, microfluidization is carried out at low pressures (e.g., about 3,500 to 7,000 or 4,000 to 6,000 pounds per square inch) to effectively meet the 6–12 micron particle size range, using 1–3 passes.

For the design of monophasic drug delivery systems of very slightly soluble drugs such as felodipine, a monophasic particle size distribution, ranging from 1–3 microns, is used to design a swellable, erosion rate-controlled drug delivery system, by using a combination of a highly swellable non-ionic polymer and hydrophilic insoluble excipients. For the design of monophasic drug delivery systems of slightly soluble drugs such as nifedipine, etodolac, and glipizide, a monophasic particle size distribution, ranging from 6–12 microns, is used to design a swellable, erosion rate-controlled drug delivery system, by using a combination of a highly swellable non-ionic polymer and hydrophilic insoluble excipients.

For the design of a bi-phasic drug delivery system of insoluble drugs in general, a discrete particle size distribution, ranging from 1–3 microns or 6–12 microns is included in a rapid release core. A second discrete particle size distribution, ranging from 15–30 microns is incorporated in a non-functional or functional coating which is applied to the core. The core and the coat are separated by an enteric or non-enteric, non-functional separation layer. For further optimization of drug release, the geometry of the drug delivery system is modified.

The geometry of the drug delivery system (e.g., the tablet), for example, at a constant polymer (binder):excipient:drug ratio, can be modified from a generally spherical matrix (e.g., diameter of 10.6 mm and thickness of 6.46 mm, approximately 288 mm$^2$) to a more cylindrical form (e.g., diameter of 12.92 mm and a thickness of 4.58 mm, approximately 342 mm$^2$) to generate a larger surface area and a shorter distance for erosion or diffusion of the delivery system. The resultant effect of this particular modification is an acceleration of matrix erosion. The success of any drug delivery system is governed by the drug absorption performance, which is in turn at least a partial function of the drug release rate and characteristics. This is particularly true where the drug permeability after oral administration is not a rate-limiting step in the process of the distribution of drug molecules in the body.

Using the process of microfluidization, an aqueous medium is selected for wet-micronization of the drug/excipients based on the particle size distribution (PSD) of the feed material (unmicronized vs. micronized) and the targeted particle size distribution of the outflow microsuspension. Then a granulating material is achieved either by having all components such as the drug, a dextrin, especially a cyclodextrin such as β-cyclodextrin, hydroxy propyl cellulose, Cremophor RH-40 a surface active agent), and Simethicone (an antifoaming agent) in the feed material or by separating the operation into two phases, namely microfluidization of the drug with water and β-cyclodextrin and subsequent blending of the outflow material with a separately prepared dispersion of hydroxy propyl cellulose in water, and finally the addition of Simethicone. This operation facilitates reduction of mean particle size of the drug and β-cyclodextrin and creates a smooth latex-like micro-suspension. In the presence of dextrins, particularly cyclodextrins, particle sizes even in the nanometer ranger (e.g., below 1000 nm, e.g., less than 500 nm, less than 400 nm, and between 20 and 1000, or between 30 and 500 nm are novel and may be produced according to the present invention (with or woithout the presence of surface active agents or surface modifying agents). The dextrins, as noted, remain as particles withoin the microfluidozed system and the products. The dextrin particles may or may not be separable from the pharmaceutical particles.

The dissolution rate of a solid is described by the Noyes-Whitney equation:

$$\frac{Dc}{dt} = k(C_s - C)$$

Where $k = \frac{DA}{Vh}$

D=diffusion coefficient
A=Surface area of the dissolving solid
V=Volume of the dissolving solid
h=Diffusion layer thickness
$C_s$=Solute concentration in the diffusion layer
C=Solute concentration in the bulk During the early phase of dissolution, $C_s \gg C$ and is essentially equal to the saturation solubility $C_s$. Under these conditions and at constant temperature and agitation, the above equation reduces to $$\frac{dc}{dt} = kC_s, \quad \text{Where } k = \frac{DA}{Vh}$$

Dissolution rate expressed in the above equation is termed the intrinsic dissolution rate and is characteristic of each solid compound in a given solvent under fixed hydrodynamic conditions. The intrinsic dissolution rate is a fixed volume of solvent generally expressed as mg dissolved in min$^{-1}$ cm$^{-2}$.

A basic problem of poorly soluble drugs is an insufficient bioavailability, which is related to low saturation solubility $C_s$ and dissolution rate dc/dt. The attempts to solubilize the drugs in micelles or with cyclodextrins are of limited success for many drugs. A better approach is to microfluidize (wet-micronize) the hydrophobic drug in the presence of optimum carriers. The primary drug particle approaches about 1–3 micron size, preferably an amorphous form, and a hydrophilic surface for optimum dissolution and absorption. The sizes described herein for particles, whether for the pharmaceuticals or for the dextrins, are non-aggregated particle sizes. Unless otherwise stated, the sizes are weight average particle sizes. The ranges may alternatively be applied to number average partyicle sizes, usually where fewer than 10% by number of the particles excede the stated average size by more than 25%.

The aqueous solubility of four model drugs such as nifedipine, glipizide, etodolac, and felodipine were respectively determined to be 0.001% at all pHs, 0.04% at pH 7.5 (almost negligible at lower pHs), 0.53% at pH 7.5 (almost negligible at lower pHs), and 0.0001% at all pHs, respectively. Intrinsic dissolution rates of these model drugs, namely, nifedipine, glipizide, etodolac, and felodipine were calculated to be in mg min$^{-1}$ cm$^{-2}$, as 0.1, 0.69, 733, and 0.00086, respectively. The media, 50 ml water using BioDis III; 900 ml phosphate buffer using Type II/paddle; 900 ml phosphate buffer using Type II/paddle, and 500 ml phosphate buffer with 1% sodium lauryl sulfate, Type II, paddle. Based on this data a 10–20 micron range for nifedipine and felodipine will exhibit dissolution rate-limited absorption. Etodolac will not exhibit dissolution rate-limited absorption and glipizide may exhibit dissolution rate-limited absorption.

The use of antifoaming agents, such as silicone compounds, fluorinated compounds, such as simethicone and FC-40 manufactured by Minnesota Mining and Manufacturing Co. (although there are many chemical classes of materials known in the art for this purpose) has already been briefly referred to. These compounds provide a significant benefit to the process performance that is unrelated to any surface active effect they may have on the relationship of the pharmaceutical to the liquid carrier in the microfluidization process. When particles are provided in the aqueous carrier, significant amounts of air or other gas is carried with the particles. Because of the small size of the particles, the air or other gas is not easily shed from the surface of the small particles, it is carried into the carrier liquid, and foaming can occur in the suspension. This is highly undesirable in the microfluidization process and adversely affects the ability of the process to control the particle size and other benefits. Therefore it is desirable, either before any microfluidization occurs or shortly after initiation of the microfluidization process, to introduce an anti-foaming agent to the particles and/or to the particles and liquid (water) carrier. It is particularly desirable to add the particles and antifoaming agent to the liquid carrier and allow a significant dwell time (e.g., at least 5 minutes, preferably at least 10 or 15 minutes, up to an hour or more) to allow the air or other gas to disassociate itself from the surface of the particles. Some mild agitation to 'shake-off' the bubble from the surface of the particles may be desirable, but is not essential. This defoaming may occur directly within a storage or feed tank for use in the microfluidization system or may be done at another time prior to introduction of the suspension into the microfluidizer. The defoaming agents, some of which are surfactants (a term that is actually quite broad in scope), may also be used, and are preferably used in amounts that are much smaller than the concentrations or volumes that are usually necessary fir effective surface active properties. For example, defoaming agents may be used in w/w/percentages of the solution in ranges, for example, of 0.0005% to 0.2%, 0.005 to 0.1%, or 0.005 to 0.08% by weight of the total solution/dispersion, while surface active agents tend to be used in much higher concentrations (even though some disclosures may include levels as low as those described herein for defoaming agents).

It is important to note that the dextrin is introduced into the carrier drug particle system as a solid particle itself. The dextrin remains as a particle in the process, even if there is some breakdown or minor dissolution of the dextrin. This is important to recognize since the dextrin cannot act as a surface modifying agent, does not form a coating on the surface of the pharmaceutical particle, and remains only non-covalently associated with the hydrophobic, water-insoluble drug particle during and after the microfluidization process. The pharmaceutical hydrophobic, relatively water-insoluble drug, the dextrin or both may be added to the suspension or used to form the suspension in any size particle, as for example, from about 1 to 50, 1 to 100, to 1 to 200 micrometers in size. The dextrin particles may be larger or smaller than the drug particles. The dextrin may be added to the drug in a ratio of drug to dextrin of from about 1:50 to 50:1. With certain of the drugs actually tested particularly practicable ranges include from 1:50 to 20:1 (drug/dextrin, particularly β-cyclodextrin), 1:30 to 5:1, 1:25 to 1:1, and 1:15 to 1:2.

Process and Apparatus For Treating Hydrophobic Drugs

The current invention is based on wet micronization of the hydrophobic drug particle in association with cyclodextrins (and optional surface active agents) using a high-pressure homogenizer known as a microfluidizer.

The components of the commercially available microfluidizer are:

a. Pump (Hydraulic Intensifier)
b. Ceramic Interaction Chamber (CIC)
c. Auxiliary Processing Module (APM)
d. Outlet Heat Exchanger The hydraulic power system provides power to the microfluidizer equipment via pressurized hydraulic fluid. The High Pressure Intensifier multiplies the pressure supplied from the hydraulic power system via the hydraulic fluid to an optimal operating level.

In the practice of the present invention, any commercial microfluidizer may be used, including, but not limited to the following microfluidizers, all supplied by Microfluidics International Corporation:

Model M110-EH, which is a laboratory scale microfluidizer which utilizes an electric hydraulic pump;

Model M-110Y, which is a laboratory scale microfluidizer equipped with a sanitary pressure transducer connected to a digital data acquisition system;

Model M-140K, which is a high pressure microfluidizer with a pressure limit of 40,000 psi; and Model M-210, which is a pilot plant microfluidizer with a pressure range from 3,000 to 30,000 psi, and with flow rates between 1.9 to 5.7 L/min. It is capable of handling a sample size of 3.8 L or greater.

The Microfluidizer M-210 EH operates at higher pressures up to 35000 psi. The process stream enters the inlet reservoir. An air-powered intensifier pumping system accelerates the process stream, propelling into a processing zone called the interaction chamber. This chamber consists of microchannels, where the process stream separates into two. It changes direction and collides into a single stream again. The size reduction of the material occurs in the Interaction Chamber (L 230 Z, 500-micron channel) and Auxiliary Processing Module (T 250 Z, 1000-micron channel). Then product is accelerated to a high velocity and is subjected to shear, impact and cavitation. This causes particles and droplets to reduce in size as small as sub-micron depending upon the processing pressure and number of cycles applied. A schematic representation of the Microfluidizer Model 210EH is shown in FIG. 1. The microfluidizer system 2 comprises a pump 4 that receives a macro-suspension of hydrophobic particles in a suspension from a container or feed reservoir 6. A pressure gauge 8 identifies the pressure of the flow of the feed solution in pipe 10 as the macro-suspension passes into an auxiliary chamber 12. The first treated macro-suspension passes from the auxiliary container 12 to the interaction chamber 14 through pipe 16. After completion of the microfluidization step, the sized particles in suspension pass through pipe 18 out of the system, with a heat exchanger 20 shown in a preferred system to enable on-line drying of the micro-suspension resulting from the microfluidization. The microfluidization process is most conveniently practiced with operating pressures between 2000 pounds per square inch (psi) and 20,000 psi to provide resulting particle sizes of the dimensions most appropriate for pharmaceutical dosing. The process will often progress with increasingly higher operating pressures in each subsequent pass, such as using from 2,000 to 6,000 psi in a first pass, 5,000 to 11,000 psi in a second pass, and from 9,000 to 20,000 psi in a third pass (if needed). Each pass will generally be higher than a previous pass, or operating pressures may remain constant or decrease, depending upon the specific results desired in the processing.

Equipment and Formulation Variables that Influence Microfluidization of Pharmaceutical Suspensions of Hydrophobic Drugs-equipment Variables Configuration of Interaction Chambers:

The size reduction of the material occurs in the Interaction Chamber (L 230 Z, 500-micron channel) and Auxiliary Processing Module (T 250 Z, 1000-micron channel). The product is accelerated to a high velocity and is subjected to shear, impact and cavitation.

Different sets of interaction/back pressure chambers provide versatility of different channel lumens of the interaction chambers and velocities where the streams combine. Chamber designs are available for suspension processing cell rupture, liposome formation, emulsion processing, and microencapsulation. These chambers can be utilized with the same base model Microfluidizer.

Operating Pressure:

The material temperature increases by 1.7° C. for every 1000 psi.

Number of Cycles or Passes:

The cycles are either discrete or continuous. If it takes 10 minutes to microfluidize the feed slurry on a discrete cycle basis, the machine will be run continuously for 30 minutes to complete three cycles.

Formulation Variables (Composition of Feed Material):

a. Binding agents
b. Surface-active agents
c. Antifoam agents
d. Cyclodextrins as co-microfluidization excipients
e. Absorption Enhancers The efficiency of the microfluidizer was increased when surface-active agents such as Cremophor RH 40 were added to a placebo-granulating medium containing hydroxy propyl cellulose as the binding agent and β-cyclodextrin as the material to be microfluidized. For example, regardless of the particle size distribution of β-cyclodextrin (micronized NMT 20 microns or unmicronized NLT 200 microns), the particle size was approximately 5 microns in each case at 8,000 psi with three discrete passes. The particle size of the dextrins used in the process may be within any available range as the size will be modified during the process. It is desired that the particle size of the dextrins, especially β-cyclodextrin, exceeds the minimum particle dimension sought in the micronization (microfluidization) process, that is at least 1.0 micrometers in all cases (and higher sizes where the objective minimum particle size is higher, e.g., 6–12 micrometers).

On the other hand, when Cremophor RH 40 was not used in the process, a placebo trial of β-cyclodextrin (unmicronized, 227.64 microns) in the presence of hydroxy propyl cellulose provided a particle diameter 90% less than 98.1 microns at 5,000 psi and 73.41 at 10,000 psi; where the number of discrete passes were three. From these results it is concluded that the surface active agent, although not critical to the practice of the micronization of hydrophobic, relatively water-insoluble drugs in the presence of dextrin (s), decreases the interfacial tension between the two solid particles (e.g., the β-cyclodextrin and the drug). This leads to possible amorphization of the drug crystal through particle-to-particle interaction during the more efficient microfluidization.

When binding agent such as hydroxy propyl cellulose was excluded for a trial containing unmicronized hydrophobic drug felodipine (NLT 75 microns) and the excipients were β-cyclodextrin (unmicronized 227.64 microns) and water, at an operating pressure of 10,000 psi and three passes, the particle size of the output material was NMT 2.8 microns for 90% of the distribution.

The surface-active agent increases the efficiency of microfluidization by wetting the feed material. Hydroxy propyl cellulose moderates the process of microfluidization by coating drug and of excipient particles, thereby decreasing the particle—particle interaction in the interaction chambers. Simethicone or other equivalent surface active agents (that is agents that alter the surface tension of the solution, as opposed to the surface modifying agents of U.S. Pat. No. 5,510,118 that coat and modify the surface properties of solids within the solution/dispersion) is highly desirable in removing entrapped air from the feed slurry if the requirement is to use micronized materials. If Simethicone is not used, it is virtually impossible to remove air from the slurry of the micronized materials. Furthermore, the process of microfluidization becomes highly inefficient because the microfluidizing power is used in micronizing air bubbles.

Particle Size Distribution of Feed Material

If the feed material contains unmicronized materials such as the drug and β-cyclodextrin, high pressure (~10,000 psi) microfluidization is essential to effectively reduce the particle size. Equally important is to use a "chiller" in this experiment because the temperatures of the output materials were known to approach 55° C.

The microfluidizer is cost-effective and efficient. A batch for microfluidization will range from 4–10 kg of a pre-microfluidization suspension. This is based on the amount of drug to be incorporated in the drug delivery system (low dose 2.5–10 mg vs. medium dose 30–90 mg vs. high dose 200–600 mg strength). The time required will depend on the number of passes. For example, micronized material using a low pressure unit will require one pass for a high dose drug, taking approximately one hour to complete the operation. In comparison, a similar operation using a jar mill will require four hours.

Also, the microfluidizer results in a greater product yield, approximately 99%. The particle size reduction, through micronization, is highly beneficial in enhancing the dissolution rates. This is attributed to significant increase in specific surface areas, as well as modification of particle surface from hydrophobic to hydrophilic. This is achieved by either the coating of hydrophobic drug particles with dissolution-enhancing materials such as β-cyclodextrin and/or by modifying the surface characteristics or with surface-active agents which reduce the drug-liquid interfacial tension.

Finally, it provides a smooth, stable, latex-like suspension with improved output material. The particle size distribution is narrow. Furthermore, the drug/excipient (dissolution enhancer) interaction is high. The standard deviation in the average particle size may also be more closely controlled than with standard mechanical mixing systems, for example, the variation in particle sizes for various materials may be controlled within ±20% of particles having less than or equal to a ±20% difference from the average particle diameter for 1–3 micrometer average diameter particles, 2–5 micrometer average diameter particles, and less than 20% of particles having less than or equal to a ±20% difference from the average particle diameter for particles having average particle diameters of between 5 and 15 micrometers (e.g., 15% of particles having less than or equal to a ±15% difference from the average particle diameter or less for particles having average diameters of 5–12 micrometers. These properties are more easily and more comfortably applied to variations in distribution of particles wherein fewer than 20% of the particles excede the average size by more than 25%, as the smaller size particles tend to be less controllable.

The microfluidization process makes it possible to create uniformly-sized particles at the 1–3 micron level so uniformity of granulation is controlled (due to its efficiency and time-saving qualities, it is more economical to use than traditional equipment) (by decreasing particle diameter, it improves stability of the suspension sprayed in the FBGD system) minimal contamination in the final product and ease of production scale-up.

Swelling/Erosion Rate Controlled Drug Delivery System

The physical model of drug release from a hydrophilic matrix (composed of hydroxy ethyl methylcellulose) is represented by initial contact of the tablet matrix with gastric fluid, whereby an uncontrolled fraction of the pharmacologically active substance is rapidly released into the gastric fluid. Subsequently, gradual hydration and gelling of the macromolecules form a viscous layer that gradually increases and forms a matrix from which the drug molecule is diffused after dissolution. All the soluble constituents present in the tablet contribute to modifying porosity throughout the release process. (P. Buri and E. Doelker "Formulation of sustained-release tablets, II. Hydrophilic Matrices", *Pharm. Acta. Helv.,* 55(7–8), 189–197 (1980).)

The kinetics of drug release from a hydrophilic matrix were derived (Lapidus and Lordi, 1966). These derivations were based on equation by Higuchi, T. (1963). The key feature of this equation is the drug release accumulates linearly proportional to $t^{1/2}$, according to the T. Higuchi equation below:

$$Q = \sqrt{\frac{D \cdot \varepsilon}{\tau}(2A - C_s) \cdot C_s \cdot t}$$

Where

Q=amount of drug released after time t per unit exposed area

D=the diffusivity of the drug in the permeating fluid t=the tortuosity factor of the capillary system ≈3

A=the total amount of the drug in the permeating fluid e=porosity of matrix $C_s$=drug solubility in the solvent penetrating the matrix The physical model of the release of hydrophobic drug from hydroxyethyl cellulose is represented by the following steps:

1. Diffusion of water into the matrix initiates the process of drug release.
2. Polymer starts swelling and it immediately controls the release of the pharmacologically active hydrophobic drug ingredient by forming a viscous, erosion rate-controlled drug delivery system.
3. Hydrophobic drug is released by a major mechanism of matrix erosion and a minor mechanism of matrix diffusion.
4. The particle size distribution or the specific surface area of the hydrophobic drug ingredient control the rate of drug dissolution and absorption.
5. The drug absorption is dissolution rate-limited when the particle diameter is above 1–2 microns.
6. The geometry (shape and size) of the matrix controls the rate of matrix erosion.

This is available in viscosity ranging from 75–150 cps, 5% (L Pharm); 4500 to 6500 cps, 2% (M Pharm); and 1,500 to 2,500 cps, 1% (H Pharm). Particle size distribution for all three is 90.0% minimum through 40 mesh; molecular weight distribution ranging from 90,000 (L Pharm) to 720,000 (M Pharm) to 1,000,000 (H Pharm).

The alternative polymer is based on several grades of hydroxy propyl methyl cellulose such as Methocel$^R$ E, F, and K (controlled release or CR grades) which are pharmacopeially and generically identified as 2910, 2906, and viscosity ranging from 4000 to 15000 cps and particle size of 200–325 mesh (55%) and 80–200 mesh (45%).

Low Solubility/High Permeability Drug Candidates

Drug candidates representing this class of compounds are of primary interest regarding application of microfluidization for achieving enhanced solubility ($C_s$) and intrinsic dissolution rates. This is accomplished by controlling the specific surface area through microfluidization as a function of time and pressure of microfluidization.

Several drugs under therapeutic categories such as analgesics (opioid), antibacterials, anticonvulsants, antihyperlipidaemics, anxiolytics, anti-inflammatories, antivirals, histamine $H_2$-receptor antagonists, calcium channel blockers, hypoglycemics, immunosuppressants, prokinetics, proton pump inhibitors, and anti-ulcerative drugs are candidates for microfluidization.

Analgesic (opioid) includes fantanyl. Antibacterial drugs include cefaclor, cefadroxil, cefradine, cefuroxime axetil, ciprofloxacin, erythromycin ethyl succinate, and pivampicillin. Anticonvulsant drug includes carbamazepine. Antihyperlipidaemic (HMG-CoA Reductase Inhibitors) drugs include clofibrate, gemfibrozil, lovastatin, pravastatin, simvastatin, and probucol. Anxiolytic drugs include alprazolam, benperidol, bromazepam, bromperidol, clobazam, clonazepam, droperidol, diazepam, lorazepam, and oxazepam. Anti-inflammatory drugs include azapropazone, benorilate, baclofen, bufexamac, fenbufen, diflunisal, ketoprofen, and mefanic acid. Antivirals include didanosine and zidovudine. Calcium channel blockers include dihydropyridine group of drugs such as amlodipine, isradipine, felodipine, nifedipine, nimoldipine, nisoldipine, and nitrendipine. Histamine $H_2$-receptor antagonists include famotidine and nizatidine. Immunosupressants include azathioprine and cyclosporin. Hypoglycemic drug example includes chloropropamide, tolazamide and glipizide. Prokinetic drug examples include metoclopramide and cisapride. Proton pump inhibitors include omeprazole and lansoprazole. Ulceratice colitis drug example includes sufasalazine.

Examples of the Preparation of the Granulating Medium

The drug delivery system of the present invention is comprised of a granulating medium prepared by the process of microfluidization and granulation prepared by the process of fluid bed granulation drying (FBGD). The granulating medium consists of a dispersion of the micronized drug and β-cyclodextrin in a dispersion without additional ingredients or with other additives such as those comprising or consisting of a non-ionic, water-soluble polymer such as Klucel LF and a non-ionic surfactant such as PEG-40 hydrogenated castor oil (Cremophor RH 40) and/or an antifoam agent such as Simethicone Emulsion.

In the present invention, primarily β-cyclodextrin is microfluidized with the drug in the presence or absence of a surface-active agent such as Cremophor RH40 and a granulating agent such as hydroxy ethyl cellulose. The purpose of using microfluidization is to enhance a non-covalent, physical interaction between β-cyclodextrin and drug molecules. This interaction will enhance the apparent solubility and dissolution rate of the primary drug particle. This enhancement in the dissolution rate is theoretically attributable to possible amorphization (at least at the surface of the particle) of the hydrophobic drug entity.

The microfluidizer efficiency is significantly improved by feeding a slurry of drug (unmicronized) and unmicronized β-cyclodextrin in water. Unmicronized materials will disperse well in water due to high bulk density and lack of entrapment of air. This finding was advantageously utilized for developing a drug delivery system of felodipine, which required a particle diameter of about 5 microns for efficient absorption in the distal portions of the gastrointestinal tract.

The micronizing efficiency is significantly decreased when the composition of the slurry (e.g., containing felodipine) is prepared in the presence of hydroxypropyl cellulose. This conclusion is drawn based on Table 1.

Preparation of the Granulation:

For granulation, two types of surface-active agents were selected and, appropriately, located either in the granulating medium or the "bowl charge". A non-ionic surface-active agent, Cremophor RH40, was selected for decreasing the interfacial tension between the hydrophobic primary drug particle and the aqueous environment surrounding it. The effect of decreasing the interfacial tension is further improved by placing hydrophobic drugs with a granulating medium, a surface-active agent, a defoaming agent, and a dissolution enhancing agent in an interaction chamber (microfluidizer). The high shear, kinetic energy impact, and cavitation forces predominate, in order to convert the drugs into a stable, latex-type microdispersion. Other non-ionic surface-active agents include poloxamers such as Pluronic F-68 and Pluronic F-108, Polysorbates 60 and 80, and Triton WR-1339 (hydrophilic-lipophilic balance ranging from 12–18). The concentration of the non-ionic surface-active agent ranges from 0% (optional) to 3%. However, the preferred concentration is 1%, based on the weight of the granulating medium. Furthermore, in the presence of the surface-active agent, the concentration of total solids in the granulating medium is, preferably, 25% w/w or lower.

Sodium lauryl sulfate (SLS) or sodium dioctyl sulfosuccinate (DOSS), anionic surface active agents in powdered form, affect the dissolution of the hydrophobic drugs either by decreasing the interfacial tension of non-ionic hydrophobic drugs or by increasing the interfacial reaction with acidic drugs such as etodolac. Since SLS or DOSS interact with hydroxypropyl cellulose to form a thick paste, SLS or DOSS are located in the "bowl charge". The concentration of powdered SLS or DOSS ranges from 0% (optional) or 0.1 to 5%. However, the preferred concentration is about 3%, based on total solids in the final, unlubricated dried granulation. When the surface-active agent is incorporate in the "bowl charge", the solids concentration of the granulating medium described above is preferred at 30% or 40% or above.

During the granulation process, hydroxyethyl cellulose (Natrosol 250 Pharm) acts as a sustained release matrix polymer. The process is controlled to prevent sloughing off of polymeric material caused by excessive swelling due to its highly swellable nature.

Controlled swellability may be achieved by using insolubles such as dicalcium phosphate, calcium phosphate and β-cyclodextrin. The matrix layer provides the structure characteristics of high cohesiveness and integrity; which it erodes uniformly over a period of 24 hours. The swellable polymer/excipients pre-mix ranges from 16/84 to 50/50 (excipients, comprised of water-insoluble materials). In these proportions, these materials are used to form the controlled swelling matrix layer of the drug.

EXAMPLES

The following examples illustrate the influence of Microfluidization on the Particle Size Distribution of hydrophobic drugs.

EXAMPLE 1

Microfluidized Suspension, Particle Diameter μm

| Therapeutic Category | Drug Molecule | Composition of Feed Material | PSD of Feed Material | Microfluidizing Control Parameters | | PSD of Output Material After Processing |
|---|---|---|---|---|---|---|
| | | | | Operating Pressure | Number of Passes | |
| | Placebo 1 | Micronized B-cyclodextrin + Klucel + Cremophor RH-40 | 5.04 | 4,000 | 1, 2, 3 | 3.06, 2.12, 1.83 |
| | | | | 8,000 | 1, 2, 3 | NA, NA, 1.98 |
| | | | | 12,000 | 1, 2, 3 | 2.69, 3.51, 3.35 |
| | Placebo 2 | Unmicronized B-cyclodextrin + Klucel + Cremophor RH-40 | 4.18 | 4,000 | 1, 2, 3 | 2.37, 0.79, 1.77 |
| | | | | 8,000 | 1, 2, 3 | 1, 84, 4.10, 7.93 |
| | | | | 12,000 | 1, 2, 3 | 2.66, 3.55, 1.79 |
| | Placebo 3 | Unmicronized B-cyclodextrin + Klucel | | 5,000 | 3 | 98.1 |
| | | | | 10,000 | 3 | 73.4 |

Note: Unmicronized β-Cyclodextrin particle diameters are 102.12 (0.9) and 47.20 (0.5). Micronized β-Cyclodextrin particle diameters are (0.9) and (0.5).

EXAMPLE 2

Microfluidized Suspension, Particle Diameter μm

| Therapeutic Category | Drug Molecule | Composition of Feed Material | PSD of Feed Material | Microfluidizing Control Parameters | | PSD of Output Material After Processing |
|---|---|---|---|---|---|---|
| | | | | Operating Pressure | Number of Passes | |
| Calcium Channel | Felodipine | Unmicronized B-cyclodextrin + | 246.93 (87.40) | 10,000 | | 44.59 (22.80) (Before adding Klucel) |

EXAMPLE 2-continued

Microfluidized Suspension, Particle Diameter μm

| Therapeutic Category | Drug Molecule | Composition of Feed Material | PSD of Feed Material | Microfluidizing Control Parameters | | PSD of Output Material After Processing |
|---|---|---|---|---|---|---|
| | | | | Operating Pressure | Number of Passes | |
| Blocker | 254.95 (86.37) | Unmicronized Felodipine + Water | | | 3 | 5.51 (1.90) (After adding Klucel) |
| | 142.48 (58.78) | Same as above | 156.77 (48.55) | 10,000 | 3 | 2.18 (1.08) (After adding Klucel) |
| Calcium Channel Blocker | Nifedipine | Micronized Nifedipine + Unmicronized B-cyclodextrin + Cremophor RH-40 + Water | 8.54 | 4,000 | 1 | 4.61 |
| | | | | 4,000 | 2 | 4.51 |
| | | | | 4,000 | 3 | 4.88 |
| Anti-Diabetic Agent | Glipizide | Micronized Glipizide + Klucel LF + Unmicronized B-cyclodextrin + Cremophor RH-40 + Water | | | 1 | |
| | | | | | 2 | |
| | | | 16.0 (7.52) | 5,000 | 3 | 7.52 (3.84) |
| | Glipizide | Micronized Glipizide + Klucel LF + Micronized B-cyclodextrin + Cremophor RH-40 + Water | | | 1 | |
| | | | | | 2 | |
| | | | 15.93 (7.60) | 5,000 psi | 3 | 12.06 (5.72) |
| Non-Steroidal Anti-Arthritic Drug (NSAID) | Etodolac | Micronized Etodolac + Klucel LF + Micronized B-cyclodextrin + Cremophor RH-40 + Water | | 5000 psi | 1 | |
| | | | | | 2 | |
| | | | | | 3 | 12.15 |

Note: Particle size distribution (PSD) values in parentheses represent the statistical diameter d (0.5) whereas without parentheses it represents d (0.9). Similar operating pressures and number of passes were used in each of these examples.

EXAMPLE 3

Glipizide Hydrophilic Matrix DDS, Batch size 40,000 Units
(Quantities are in mg)

| Ingredients | Matrix A | Matrix B | Matrix C | Matrix D |
|---|---|---|---|---|
| Hydroxypropyl Cellulose, NF | 6.000 | 6.000 | 6.000 | 6.000 |
| Polyoxyl 40 Hydrogenated Castor Oil, NF | 1.875 | 1.875 | 1.875 | 1.875 |
| Glipizide, USP MICRONIZED | 5.000 | 5.000 | 5.000 | 5.000 |
| β-Cyclodextrin, USP | 35.500 Micronized | 35.500 Micronized | 35.500 Unmicronized | 35.500 Unmicronized |
| Simethicone, USP | 0.095 | 0.095 | 0.095 | 0.095 |
| Dibasic Calcium Phosphate Dihydrate, USP | 71.000 | 71.000 | 71.000 | 71.000 |
| β-Cyclodextrin, USP UNMICRONIZED | 49.800 | 43.600 | 49.800 | 43.600 |
| Hydroxyethyl Cellulose, NF | 35.200 | | 35.200 | |
| Hydroxypropyl methyl Cellulose, NF | | 41.400 | | 41.400 |
| Un-lubricated granulation, Sub-Total | 204.47 | 204.47 | 204.47 | 204.47 |
| Lubricated granulation, | 207.74 | 207.74 | 207.74 | 207.74 |

| GENERAL PROCEDURE |
| --- |
| 01* Into a S.S. Container equipped with stirrer add 1880 g Purified water. Add 264 g Hydroxypropyl cellulose, NF, EP, JP (Klucel LF) under stirring until a smooth paste is formed. Add 82.5 g of polyoxyl 40 hydrogenated castor oil and mix. |
| 02* Into the container above, add 1880 g Purified water. Add 220 g micronized glipizide, USP under stirring. Add 1880 g Purified Water. Add 1562 g β cyclodextrin, either un-micronized or micronized, and mix to get a uniform slurry. Finally, add 4.180 g Simethicone Emulsion. |
| 03 Start passing the dispersion from Step No. 2 through a Microfluidizer (M-210 EH) at 5,000 psi, three discrete passes. |
| 04 Submit dispersion samples, with and without microfluidization, for PSD analysis using Mastersizer ®. |
| 05 Transfer the drug dispersion from Step No. 3 in a measuring cylinder. Place measuring cylinder on the magnetic stirrer with magnet in measuring cylinder. Connect the measuring cylinder to Glatt (GPCG-5) through a peristaltic pump. |
| 06 Charge 2840 g Dicalcium Phosphate Dihydrate, 1744 or 1922 g un-micronized β cyclodextrin, 1408 g Hydroxyethyl Cellulose (Natrosol 250 M) or 1656 g Hydroxypropyl methylcellulose (Methocal E4 M PCR) into GPCG-5 granulator container. |
| 07 Using an appropriate air volume, inlet temperature and spray rate granulate the material from Step No. 6 using "Required amount of drug dispersion to spray" from step no. 5. |
| 08 When drug dispersion spray is completed purge Purified water. Dry the granules to the moisture content not more than 2%. |
| 09 When the moisture content is less than 2% stop drying and discharge the product. Unload the granules in double transparent polybags kept in black polybag. |
| 10 Add Stearic acid, Colloidal silicon dioxide (Aerosil) and Magnesium stearate to granules of Step 09 and mix. |
| 11 Compress the lubricated granules form Step No. 14 into tablets using compression machine using 8 mm SC punches. |

*10% w/w excess.

EXAMPLE 4

Felodipine Hydrophilic Matrix DDS, Batch size 17,496 units
(Quantities are in mg)

| Ingredients | Matrix A | Matrix B | Matrix C | Matrix D |
| --- | --- | --- | --- | --- |
| Felodipine BP | 5.000 | 5.000 | 5.000 | 5.000 |
| β-Cyclodextrin, USP | 84.971 | 84.971 | 84.971 | 84.971 |
| Hydroxypropyl Cellulose, NF | 13.717 | 13.717 | 13.717 | 13.717 |
| Simethicone Emulsion | 0.05 | 0.05 | 0.05 | 0.05 |
| Dibasic Calcium Phosphate Dihydrate, USP | 162.323 | 162.323 | 162.323 | 149.754 |
| β-Cyclodextrin, USP | 125.743 | 125.743 | 125.743 | 113.174 |
| Hydroxyethyl Cellulose, NF | 68.587 | | 68.587 | |
| Hydroxypropylmethyl Cellulose, NF | | 68.587 | | 93.725 |
| Unlubricated Granulation, Sub-Total | 460.391 | 460.391 | 460.391 | 460.391 |
| Lubricated granulation, Sub-Total | 467.757 | 467.757 | 467.757 | 467.757 |

| GENERAL PROCEDURE |
| --- |
| 01* Into a S.S. Container equipped with stirrer add 1260 g Purified water. Add Hydroxypropyl cellulose, NF, EP, JP (Klucel LF) under stirring. Stir for five minutes and keep it for soaking for 2 hours. After soaking mix till uniform dispersion is formed. |
| 02* Into another S.S. Container equipped with stirrer add 1880 g Purified water. Add Felodipine BF under stirring. Add unmicronized β-cyclodextrin, mix to get a uniform slurry. |
| 03 Start passing the dispersion from Step No. 2 through a Microfluidizer (M-210 EH) at 10,000 psi, three passings. |
| 04 Add Klucel mucilage of Step 1 to dispersion of Step 3. Rinse the container with Purified Water. Add 8.748 g Simethicone emulsion. Mix till uniform dispersion is formed. QS (quantum sufficient) with water to 6200 g. |
| 05 Transfer the drug dispersion from step no. 4 in a measuring cylinder. Place measuring cylinder on the magnetic stirrer with magnet in |

-continued

GENERAL PROCEDURE

| | |
|---|---|
| | measuring cylinder. Connect the measuring cylinder to Glatt (GPCG-5) through a peristaltic pump. |
| 06 | Charge 2840 g Dicalcium Phosphate Dihydrate for Matrices A, B, C, and 2620 g for D; 2200 β-cyclodextrin for Matrices A, B, C and 1980 g for D; 1200 g Hydroxyethyl Cellulose (Natrosol 250 M) for Matrices A and C; 1200 g Hydroxypropyl methylcellulose (Methocel E4 M PCR) for Matrix B and 1640 g for D, into GPCG-5 granulator container. |
| 07 | Using an appropriate air volume, inlet temperature and spray rate granulate the material from Step No. 6 using "Required amount of drug dispersion to spray" from Step No. 5. |
| 08 | When drug dispersion spray is completed purge Purified water. Dry the granules to the moisture content of not more than 2%. |
| 09 | When the moisture content is less than 2% stop drying and discharge the product. Unload the granules in double transparent polybags kept in black polybag. |
| 10 | Add Stearic acid, Colloidal silicon dioxide (Aerosil) and Magnesium stearate to granules of Step No. 9 and mix. |
| 11 | Compress the lubricated granules from Step No. 10 into tablets using compression machine using 11 mm SC punches. |

*10% w/w excess.

EXAMPLE 5

Nifedipine Hydrophilic Matrix DDS, Batch Size 6878 Units
(Quantities are in mg)

| Ingredients for Label Claim | Matrix A 30 mg | Matrix B 60 mg | Matrix C 90 mg |
|---|---|---|---|
| Hydroxypropyl Cellulose, NF | 3.780 | 7.560 | 11.340 |
| Polyoxyl 40 Hydrogenated Castor Oil, NF | 2.380 | 4.760 | 7.140 |
| Nifedipine, USP MICRONIZED | 30.000 | 60.000 | 90.000 |
| β-Cyclodextrin, USP UNMICRONIZED | 16.180 | 32.360 | 48.540 |
| Simethicone, USP | 0.100 | 0.200 | 0.300 |
| Dibasic Calcium Phosphate Dihydrate, USP | 76.000 | 152.000 | 228.000 |
| β-Cyclodextrin, USP UNMICRONIZED | 60.000 | 120.000 | 180.000 |
| Hydroxyethyl Cellulose, NF | 80.000 | 160.000 | 240.000 |
| Un-lubricated granulation, Sub-Total | 268.440 | 536.880 | 805.320 |
| Lubricated granulation | 272.2 | 544.4 | 816.6 |
| Functional Coat Weight Gain based on specific surface area | | | |
| Non-Functional Color Coat for protection from white light Weight Gain based on specific surface area | | | |

GENERAL PROCEDURE

| | |
|---|---|
| 01* | Into a S.S. Container equipped with stirrer add 1236.6 g Purified water. Add 163.7 g Hydroxypropyl cellulose, NF, EP, JP (Klucel LF) under stirring until a smooth paste is formed. Add 103.2 g of polyoxyl 40 hydrogenated castor oil and mix. |
| 02* | Into the container above, add 1234.8 g Purified water. Add 1299.9 g micronized nifedipine USP (specific surface area of 4.5 m²/g, under stirring. Add 4907.2 g Purified Water. Add 701.0 g unmicronized β-cyclodextrin. Mix to get a uniform slurry. Finally, add 14.2 g Simethicone Emulsion. |
| 03 | Start passing the dispersion from Step No. 2 through a Microfluidizer (M-210 EH) at 5,000 psi, three discrete passes. |
| 04 | Submit dispersion samples, with and without microfluidization, for PSD analysis using Mastersizer ®. |
| 05 | Transfer the drug dispersion from Step No. 3 in a measuring cylinder. Place measuring cylinder on the magnetic stirrer with magnet in measuring cylinder. Connect the measuring cylinder to Glatt (GPCG-5) through a peristaltic pump. |
| 06 | Charge 3137.1 g Dicalcium Phosphate Dihydrate, 2467.9 g unmicronized β-cyclodextrin, 3300 g Hydroxyethyl Cellulose (Natrosol 250 M) into GPCG-5 granulator container. |
| 07 | Using an appropriate air volume, inlet temperature and spray rate granulate the material from Step No. 6 using "Required amount of drug |

| GENERAL PROCEDURE |
|---|
| dispersion to spray" from Step No. 5. |
| 08 When drug dispersion spray is completed purge Purified water. Dry the granules to the moisture content of not more than 2%. |
| 09 When the moisture content is less than 2% stop drying and discharge the product. Unload the granules in double transparent polybags kept in black polybag. |
| 10 Add Stearic acid, Colloidal silicon dioxide (Aerosil) and Magnesium stearate to granules of Step No. 9 and mix. |
| 11 Compress the lubricated granules from Step No. 10 into tablets using compression machine using 8 mm round SC punches, 13 mm round SC punches, and 19 mm × 11 mm oval SC punches, respectively for 30, 60, and 90 mg. |
| 12 Apply functional coating based on specific surface area of the specific strength. |
| 13 Apply non-functional color coat to protect the drug from white light. |

*10% w/w excess.

EXAMPLE 6

Nifedipine Biphasic Drug Delivery System, 60 mg, 6878 Units (Quantities are in mg)

| Ingredients | Core | Drug Coat | Color Coat |
|---|---|---|---|
| Nifedipine, USP, 0.5 m²/g SSA | | 30.000 | |
| Nifedipine, USP, 4.5 m²/g SSA | 30.000 | — | |
| Hydroxypropyl Cellulose, NF | 3.780 | — | |
| Polyoxyl 40 hydrogenated Castor Oil | 2.380 | — | |
| Simethicone, USP | 0.100 | 0.100 | |
| β-Cyclodextrin, USP Unmicronized | 26.000 | 26.000 | |
| Dibasic Calcium Phosphate Dihydrate, USP | 76.000 | — | |
| β-Cyclodextrin, USP Unmicronized | 50.000 | — | |
| Hydroxyethyl Cellulose, NF (Natrosol ® 250 L Pharm) | 80.000 | 5.000 | |
| Polyethylene Glycol 400 | — | 0.500 | |
| Unlubricated granulation, Sub-Total | 268.260 | — | |
| Lubricated granulation, Sub-Total (1.016% of Lubricated) Core Weight | 272.000 | — | |
| Drug Coat Weight | — | 61.600 | 333.6 |
| Sub-Total Core + Drug Coat | — | — | |
| Non-Functional Color Coat for protection from white light | | | 343.6 |
| 3% Weight Gain added on to Drug Coated Core | | | |

| GENERAL PROCEDURE |
|---|
| 01* Into a S.S. Container equipped with stirrer add 619.4 g Purified water. Add 91.85 g Hydroxypropyl cellulose, NE, EP JP (Klucel LF) under stirring until a smooth paste is formed. Add 51.6 g of polyoxyl 40 hydrogenated castor oil and mix. |
| 02* Into the container above, add 617.4 g Purified water. Add 649.95 g micronized nifedipine USP (specific surface area of 4.5 m²/g, under stirring. Add 2453.6 g Purified Water. Add 350.5 g unmicronized β-cyclodextrin. Mix to get a uniform slurry. Finally, add 7.1 g Simethicone Emulsion. |
| 03 Start passing the dispersion from Step No. 2 through a Microfluidizer (M-210 EH) at 5,000 psi, three discrete passes. |
| 04 Submit dispersion samples, with and without microfluidization, for PSD analysis using Mastersizer ®. |
| 05 Transfer the drug dispersion from Step No. 3 in a measuring cylinder. Place measuring cylinder on the magnetic stirrer with magnet in measuring cylinder. Connect the measuring cylinder to Glatt (GPCG-5) through a peristaltic pump. |
| 06 Charge 1568.55 g Dicalcium Phosphate Dihydrate, 1243.95 g unmicronized β-cyclodextrin, 1650 g Hydroxyethyl Cellulose (Natrosol 250 L) into GPCG-5 granulator container. |

-continued

| | GENERAL PROCEDURE |
|---|---|
| 07 | Using an appropriate air volume, inlet temperature and spray rate granulate the material from Step No. 6 using "Required amount of drug dispersion to spray" from Step No. 5. |
| 08 | When drug dispersion spray is completed purge Purified water. Dry the granules to the moisture content of not more than 2%. |
| 09 | When the moisture content is less than 2% stop drying and discharge the product. Unload the granules in double transparent polybags kept in black polybag. |
| 10 | Add Stearic acid, Colloidal silicon dioxide (Aerosil) and Magnesium stearate to granules of Step No. 9 and mix. |
| 11 | Compress the lubricated granules from Step No. 10 into tablets using compression machine using 8 mm round SC punches. |
| 12 | Apply drug coating. |
| 13 | Apply non-functional color coat to protect the drug from white light. |

*10% w/w excess.

EXAMPLE 7

Etodolac Hydrophilic Matrix Drug Delivery System, 400 mg
(Quantities are in mg)

| Ingredients | Matrix A | Matrix B | Matrix C |
|---|---|---|---|
| Hydroxypropyl Cellulose, NF | 31.819 | 31.819 | 31.819 |
| Polyoxyl 40 Hydrogenated Castor Oil, NF | 20.046 | 20.046 | 20.046 |
| Simethicone Emulsion 30% | 0.901 | 0.901 | 0.901 |
| Etodolac micronized | 400.000 | 400.000 | 400.000 |
| β-Cyclodextrin, USP MICROMZED | 62.684 | 62.684 | 62.684 |
| Dibasic Calcium Phosphate Dihydrate, USP | 53.106 | 31.414 | 53.106 |
| Dibasic Sodium Phosphate, Anhydrous, USP | 53.106 | 74.798 | 53.106 |
| β-Cyclodextrin, USP | 53.096 | 53.096 | 53.096 |

EXAMPLE 7-continued

Etodolac Hydrophilic Matrix Drug Delivery System, 400 mg
(Quantities are in mg)

| Ingredients | Matrix A | Matrix B | Matrix C |
|---|---|---|---|
| UNMICRONIZED | | | |
| Hydroxyethyl Cellulose, NF (Natrosol ® 250 M) | 62.008 | 62.008 | 58.361 |
| Hydroxyethyl Cellulose, NF (Natrosol ® 250 L) | 10.943 | 10.943 | 14.590 |
| Un-lubricated granulation, Sub-Total | 747.709 | 747.709 | 747.709 |
| Lubricated granulation, Sub-Total (1.014% of Lubricated) | 758.176 | 758.176 | 758.176 |
| Non-Functional Color Coat (15% Dispersion) 3% Weight Gain | 780.921 | 780.921 | 780.921 |

| | GENERAL PROCEDURE |
|---|---|
| 01* | Into a S.S. Container equipped with stirrer add 3361.1 g Purified water. Add 427.1 g Hydroxypropyl cellulose, NE, EP, JP (Klucel LF) under stirring until a smooth paste is formed. Add 269.1 g of polyoxyl 40 hydrogenated castor oil and mix. |
| 02* | Into the container above, add 3361.1 g Purified water. Add 4907.2 g Purified Water. Add 40.3 g Simethicone Emulsion. Add 5369.4 g micronized etodolac under stirring. Add 841.4 g micronized β-cyclodextrin. Mix to get a uniform slurry. |
| 03 | Start passing the dispersion from Step No. 2 through a Microfluidizer (M-210 EH) at 5,000 psi, three discrete passes. |
| 04 | Submit dispersion samples, with and without microfluidization, for PSD analysis using Mastersizer ®. |
| 05 | Transfer the drug dispersion from Step No. 3 in a measuring cylinder. Place measuring cylinder on the magnetic stirrer with magnet in measuring cylinder. Connect the measuring cylinder to Glatt (GPCG-5) through a peristaltic pump. |
| 06 | Charge 648.1 g Dicalcium Phosphate Dihydrate, 648.1 g Dibasic Sodium Phosphate Anhydrous, 647.9 g unmicronized β-cyclodextrin, 756.7 g Hydroxymethyl Cellulose (Natrosol 250 M Pharm), and 133.5 g Hydroxyethyl Cellulose (Natrosol 250 L Pharm) into GPCG-5 granulator container. |

-continued

GENERAL PROCEDURE

| 07 | Using an appropriate air volume, inlet temperature and spray rate granulate the material from Step No. 6 using "Required amount of drug dispersion to spray" from Step No. 5. |
| --- | --- |
| 08 | When drug dispersion spray is completed purge Purified water. Dry the granules to the moisture content of not more than 2%. |
| 09 | When the moisture content is less than 2% stop drying and discharge the product. Unload the granules in double transparent polybags kept in black polybag. |
| 10 | Add Stearic acid, Colloidal silicon dioxide (Aerosil) and Magnesium stearate to granules of Step No. 9 and mix. |
| 11 | Compress the lubricated granules from Step No. 10 into tablets on a compression machine provided with pre-compression capability, using 19 mm × 11 mm Oval SC tooling. |
| 12 | Apply a weight gain of 3% using an appropriate Coating Dispersion (preferably Opadry II, 15% w/w). |

*10% w/w excess.

A non-ionic water-soluble polymer such as Natrosol 250 Pharm. provides a viscosity ranging from 75–150 cps; 5% (L Pharm), 4,500 to 6,500 cps; 2% (M Pharm); and/or 1,500 to 2,500 cps, 1% (H Pharm). Particle size distribution for all three is 90.0% min. though 40 mesh; molecular weight distribution ranges from 90,000 (L Pharm) to 720,000 (M Pharm) to 1,000,000 (H Pharm). Natrosol 250 M Pharm is preferred because it provides a suitable structure for 24-hour drug delivery system and does not have to be blended with other polymers.

Controlled swellable polymers may be used in the core matrix in quantities ranging from approximately 10 to 40%, preferably 20 to 30% by weight, based on the total weight of the hybrid core matrix excluding weight of filler and surface-active agent.

The monophasic drug delivery system for felodipine (slightly soluble, prandial-independent, and pH-independent) is developed by microfluidizing to particle diameters of about 1–2 microns for optimum absorption using hydroxy propyl cellulose (binding agent). Felodipine is suitable for the monophasic once-a-day erosion rate-controlled drug delivery because it demonstrates excellent In-vitro/in vivo correlation. It is strictly dependent on in vivo erosion of an optimally permeable particle size and is not influenced by food.

The monophasic drug delivery system for nifedipine (slightly soluble, prandial-independent, and pH-independent) is developed by microfluidizing to particle diameters of about 2–10 microns for optimum absorption using hydroxyethyl cellulose. Nifedipine is suitable for erosion rate-controlled drug delivery with highly swellable hydroxypropyl cellulose because of its swellability and slightly prolonged gastric retention creating a pseudo-fed condition and enhances the time for drug dissolution, and thereby enhances drug absorption by saturating the sites related to intestinal metabolism. Additionally, it will create prandial-independence by generating equivalent responses between fasted and fed conditions in terms of Cmax and Tmax. As the solubility is about 10 times that of felodipine, the particle size range can be suitably controlled between 2–5 microns instead of 1–2 microns, in order not to create excessive hypotension in normal volunteers during Phase 1 clinical testing.

As etodolac solubility is strictly pH-dependent (0.001% at pH 1 and 0.01% at pH 5), a buffer such as dibasic sodium phosphate is required to design a pH-independent drug delivery system. Additionally, it is equally appropriate to deliver a particle of about 10 microns throughout the entire GI tract as the drug is relatively hydrophobic.

Biphasic drug delivery systems are developed two ways depending on the site-specific permeability/absorption of the drug molecule. Slow release/rapid release drug delivery of biphasic nifedipine drug delivery system is an example.

The rationale for providing a rapid release or "burst effect" in the distal part of the intestinal tract is based on relatively lower absorption rate compared to jejunum. The absorption rate of nifedipine calculated by deconvolution of the individual plasma curves was always highest from the jejunum, $t_{80\%}$ less than 0.7 hours, whereas $t_{80\%}$ from the descending colon was 1.9 to 4.5 hours and $t_{80\%}$ in the descending colon was 1.0 to 3.5 hours.

Nifedipine behaves differently from the closely related drugs nitrendipine and felodipine which show impaired absorption from the colon. (H. Bode et al., Investigation of Nifedipine absorption in different regions of the human gastrointestinal (GI) tract after simultaneous administration of $^{13}C$ and $^{12}C$-nifedipine, Euro. Journal Clin. Pharmacol., 50, 195–201 (1996).)

An example of biphasic release include drugs such as nifedipine which are more efficiently absorbed by providing a "rapid release effect" at the distal segment of the GI tract in order to equalize and overcome any hindrance to drug absorption due to intestinal metabolism or entrapment into deeper intestinal segments. A slow release delivery is presented to the proximal segment of the GI tract where absorption rates are the highest, especially in the jejunum. Refer to Example 6 as a rationale basis for nifedipine biphasic drug delivery design.

The product is designed by first preparing a core for immediate delivery of microfluidized drug particles (3 passes, 1–3 microns). This is accomplished by standard pharmaceutical operations such as fluid bed granulation of a mixture of pharmaceutically acceptable excipients using a granulating medium prepared by microfluidizing micronized drug (jet-milled) along with micronized β-cyclodextrin, a non-ionic surface active agent such as Cremophor RH-40 and simethicone. The role of simethicone is to remove air bubbles from the pre-microfluidized granulating medium. The air bubbles are created by the addition of micronized drug and β-cyclodextrin. If the air bubbles are not removed, the microfluidizer will produce micro-bubbles that will entrap the microsuspension and thereby producing granulations of unacceptably low bulk density.

The core is enteric coated to separate the immediate release component from the slow release component which is prepared to include a non-microfluidized granulating medium (ranging from 30–50 microns).

Biphasic drug delivery system of nifedipine (U.S. Pat. No. 4,892,741) describes a compression-coated tablet in which the rapid-release core of the coated tablets contains the active compound in an amorphous form or a finely grounded or micronized crystalline form. Furthermore, it points out that the coated tablet differs due to the coating containing the active compound in slow-release form and the core containing the active compound in rapid-release form.

The process of microfluidization, used for preparation of the granulating medium in the present invention, as described in Examples 1 and 2, is the preferred method for creating a drug suspension of drugs with high permeability indices but low solubility. This is achieved by converting the micronized or unmicronized drug particle, using a specific feed material composition, into a predetermined microparticulate size (between the range of 1.0 to 15 micrometers) for optimum rate of delivery (slow vs. pulsatile) resulting in optimum bioavailability.

Optimization is further achieved by geometric design. After completion of the granulating process, the granulation material is lubricated and compressed, using specialized tooling to produce the specific shape for optimum rate of drug delivery of tablets of various strengths.

Also, the microfluidization process is cost effective and efficient. It results in greater product yield, improving the quality of the output material with discrete (1–5 micron, 6–12 micron, and 15–30 microns) and narrow particle size distribution. The process ensures uniformity of granulation is well controlled. It is more economical to use than traditional equipment. It improves stability of the suspension sprayed in the FBGD system. Finally, there is minimal contamination and ease of production scale-up. The particles are also believed to have a core of crystalline (pharmaceutical) material and a shell (although not of uniform thickness) of amorphous (pharmaceutical) material as a result of the unique process.

What is claimed is:

1. A process for preparing a pharmaceutically active material having an average particle size of from about 1.0 to 15.0 micrometers comprising microfluidizing a composition comprising particulates of a water-insoluble pharmaceutical material, having a solubility of less than 15 mg/ml in an aqueous carrier liquid in the presence of at least 0.01% by weight cyclodextrin particles.

2. A process for preparing a pharmaceutically active material having an average particle size of from 10 to 1500 nm comprising microfluidizing a composition comprising particulates of a water-insoluble pharmaceutical material, having a solubility of less than 15 mg/ml, in an aqueous carrier liquid in the presence of at least 0.01% by weight of cyclodextrin particles until a particle size range of from 10 to 1500 nm is attained for the pharmaceutically active material.

3. The process of claim 1 wherein said cyclodextrin comprises β-cyclodextrin.

4. The process of claim 1 wherein the particulates are selected from the group consisting of hydrophobic glipizide, hydrophobic nifedipine (30–90 mg), and hydrophobic etodolac and the particulates are present with the cyclodextrin in a pre-blended dispersion of a binding agent, a non-ionic surface active agent and water, along with a dissolution enhancing excipient and microfluidizing said composition to create a microsuspension having suspension particles with an average diameter for the pharmaceutical particulates of between 1.0 and 15 micrometers.

5. The process of claim 3 wherein the particulates are selected from the group consisting of hydrophobic glipizide, hydrophobic nifedipine (30–90 mg), and hydrophobic etodolac and the particulates are present with the cyclodextrin in a pre-blended dispersion of a binding agent, a non-ionic surface active agent and water, along with a dissolution enhancing excipient and microfluidizing said composition to create a microsuspension having suspension particles with an average diameter for the pharmaceutical particulates of between 1.0 and 15 micrometers.

6. The process of claim 1, wherein a binder is present during microfluidization of the particulates.

7. The process of claim 6 wherein said binder comprises a low viscosity polymer.

8. The process of claim 7 wherein said binder comprises hydroxy propyl cellulose.

9. The process of claim 8 wherein said hydroxy propyl cellulose is present in a 1–5% weight/weight ratio of all solids within said composition that is microfluidized.

10. The process of claim 9 wherein said hydroxy propyl cellulose is present as from 2–3% w/w of all solid materials that are microfluidized.

11. The process of claim 1, wherein a surface-active agent is present during microfluidization of said composition.

12. The process of claim 11 wherein said surface-active agent comprises a non-ionic surface-active agent.

13. The process of claim 12 wherein said non-ionic surface-active agent comprises polyoxyl hydrogenated castor oil in a 0.5–3% w/w ratio of the solids that are microfluidized.

14. The process of claim 1 wherein a defoaming agent is added to the materials prior to microfluidization.

15. The process of claim 1 wherein the cyclodextrin is selected from the group consisting of α-Cyclodextrin, β-Cyclodextrin, dimethyl-β-Cyclodextrin and hydroxy ethyl-β-cyclodextrin.

16. The process of claim 15 wherein β-cyclodextrin is present as 10–50% w/w of an active core of a delivery system.

17. The process of claim 16 wherein in the presence of glipizide, the β-cyclodextrin is present as 25–45% by weight; in the presence of nifedipine the β-cyclodextrin is present as from 10–30%, and in the presence of etodolac the β-cyclodextrin is present as 5–25% w/w of solids in a core of a delivery system.

18. The process of claim 1 wherein β-Cyclodextrin is present as from 10 to 50% by weight of a core of a delivery system.

19. The process of claim 18 wherein said composition also comprises dicalcium phosphate dihydrate as from 25–40% by weight of the total solids in said composition.

20. The process of claim 18 wherein said composition also comprises a highly swellable polymer in an amount comprising from 10 to 40% by weight of solids that are microfluidized.

21. The process of claim 19 wherein said highly swellable polymer comprises hydroxyethyl cellulose.

22. The process of claim 18 wherein said composition also comprises disodium phosphate as a buffering agent, ranging from 5–10% of the composition that is microfluidized.

23. The process of claim 1 wherein said microfluidization is performed in the presence of hydrophobic felodipine and in the absence of surface-active agents.

24. The process of claim 1 wherein said microfluidization is performed in the absence of hydroxypropyl cellulose.

25. The process of claim 24 wherein said microfluidization is performed in the presence of hydrophobic felodipine and in the absence of hydroxypropyl cellulose.

26. The process of claim 2 wherein said cyclodextrin comprises β-cyclodextrin.

27. The process of claim 26 wherein said particulates are selected from the group consisting of hydrophobic glipizide, hydrophobic nifedipine, and hydrophobic etodolac.

28. The process of claim 27 wherein the particulates are present with the cyclodextrin in a pre-blended dispersion of a binding agent, a non-ionic surface active agent and water, along with a dissolution enhancing excipient and microfluidizing said composition to create a microsuspension having suspension particles with an average diameter for the pharmaceutical particulates of between 10 and 1500 nanometers.

* * * * *

UNITED STATES PATENT AND TRADEMARK OFFICE
CERTIFICATE OF CORRECTION

PATENT NO.     : 6,555,139 B2
DATED          : April 29, 2003
INVENTOR(S)    : Sharma It is certified that error appears in the above-identified patent and that said Letters Patent is hereby corrected as shown below:

<u>Title page,</u>
Item [56], References Cited, FOREIGN PATENT DOCUMENTS, delete "0540158" and insert -- 0240158 --, therefor.
Delete "1/1987" and insert -- 10/1997 --, therefor.
Delete "a1" and insert -- A1 --, therefor.
U.S. PATENT DOCUMENTS, delete "Brandstroom" and insert -- Brandstrom --, therefor.
Delete "Elge" and insert -- Elger --, therefor.
Delete "4,960,105" and insert -- 4,962,105 --, therefor.
Delete "4,960,482" and insert -- 4,960,782 --, therefor.
Delete "et al." after "Remington".
Insert the following under "4,968,808 A   11/1990  Mosdorf et al. ……….. 548/205":
-- 4,973,469 A   11/1990  Mulligan et al. ……….. 424/461 --.
Delete "427/213.16" and insert -- 427/213.36 --, therefor.
Delete "Martin" and insert -- Martini --, therefor.
Delete "Loverecich" and insert -- Lovrecich --, therefor.
Delete "414/480" and insert -- 424/480 --, therefor.
Delete "Bustti" and insert -- Busetti --, therefor.
Delete "Sergent" and insert -- Sargent --, therefor.
Delete "Biachwall" and insert -- Baichwal --, therefor.

<u>Column 3,</u>
Line 25, delete "ODRVs)" and insert -- (DRVs) --, therefor.

<u>Column 9,</u>
Line 51, insert -- ( -- before "a".
Line 65, delete "woithout" and insert -- without --, therefor.
Line 67, delete "withoin" and insert -- within --, therefor; and delete "microfluidozed" and insert -- microfluidized --, therefor.

<u>Column 10,</u>
Line 45, delete "excede" and insert -- exceed --, therefor.

<u>Column 11,</u>
Line 33, delete "fir" and insert -- for --, therefor.

<u>Column 14,</u>
Line 66, delete "excede" and insert -- exceed --, therefor.

UNITED STATES PATENT AND TRADEMARK OFFICE
CERTIFICATE OF CORRECTION

PATENT NO. : 6,555,139 B2
DATED : April 29, 2003
INVENTOR(S) : Sharma

It is certified that error appears in the above-identified patent and that said Letters Patent is hereby corrected as shown below:

Column 26,
Line 2, under "General Procedure", delete "NE" and insert -- NF --, therefor.

Column 28,
Line 2, under "General Procedure", delete "NE" and insert -- NF --, therefor.

Signed and Sealed this

Ninth Day of December, 2003

JAMES E. ROGAN
*Director of the United States Patent and Trademark Office*